United States Patent
Aynsley-Green et al.

(10) Patent No.: US 6,372,501 B1
(45) Date of Patent: Apr. 16, 2002

(54) GLUCOSE RESPONSIVE BETA-CELL LINE

(75) Inventors: Albert Aynsley-Green, London; Keith Lindley, Surrey; Kevin Docherty, Oya; Mark Dunne, Sheffield; Wendy MacFarlane, Newcastle-upon-Tyne; Roger Frank Lever James, Leicester, all of (GB)

(73) Assignees: Aberdeen University, Aberdeen; The University of Sheffield, Sheffield; The University of Leicester, Leicester; University College London, London, all of (GB)

( * ) Notice: Subject to any disclaimer, the term of this patent is extended or adjusted under 35 U.S.C. 154(b) by 0 days.

(21) Appl. No.: 09/486,975
(22) PCT Filed: Sep. 3, 1998
(86) PCT No.: PCT/GB98/02648
  § 371 Date: May 4, 2000
  § 102(e) Date: May 4, 2000
(87) PCT Pub. No.: WO99/11759
  PCT Pub. Date: Mar. 11, 1999

(30) Foreign Application Priority Data

Sep. 4, 1997 (GB) .............................. 9718844

(51) Int. Cl.[7] .............................. C12N 15/63
(52) U.S. Cl. .................. 435/455; 435/325; 435/366; 435/382; 435/383; 435/391; 435/440; 435/465

(58) Field of Search .................. 435/325, 366, 435/382, 383, 341, 440, 375, 455, 465; 424/93.21

(56) References Cited

U.S. PATENT DOCUMENTS 5,780,299 A * 7/1998 Coon et al. .................. 435/366
5,821,121 A * 10/1998 Brothers ...................... 435/325

OTHER PUBLICATIONS

See Boutin et al (Bio Techniques 23(3): 358–360, Sep. 1997) See Abstract.*
See Kukuvitis et al (J. Clin. Endocrinol. Metab. 82(4): 1192–1194, Apr. 1997). See Abstract.*

* cited by examiner

Primary Examiner—James Ketter
Assistant Examiner—Richard Schnizer
(74) Attorney, Agent, or Firm—Licata & Tyrrell P.C.

(57) ABSTRACT

The present invention provides an immortalized insulin producing human β-cell which may be rendered glucose responsive by suitable bioengineering methods. The invention also provides a method for producing an immortalized glucose responsive insulin producing human β-cell comprising the steps of selecting an unregulated immortalized human insulin secreting β-cell, transecting said selected cell line with elements for the genetic control of glucose responsiveness and proliferating said transfected β-cell accordingly.

9 Claims, 19 Drawing Sheets

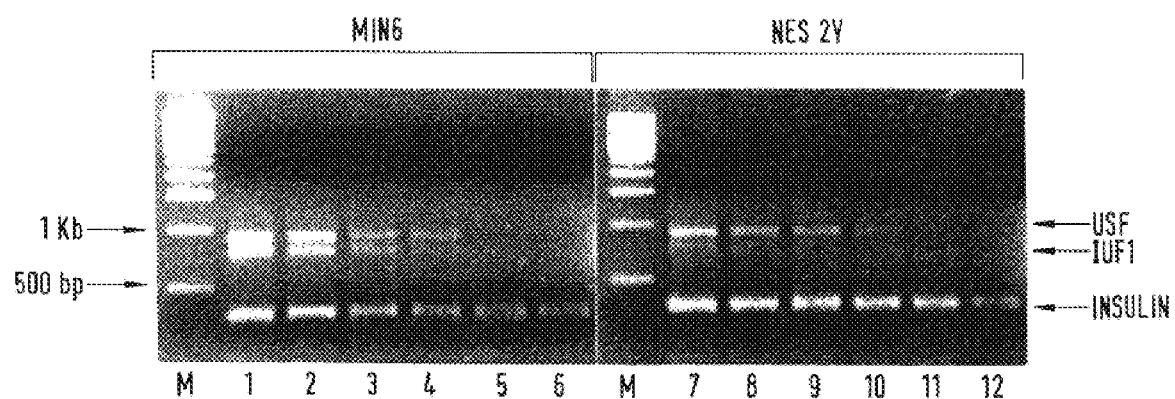

Figure 1:
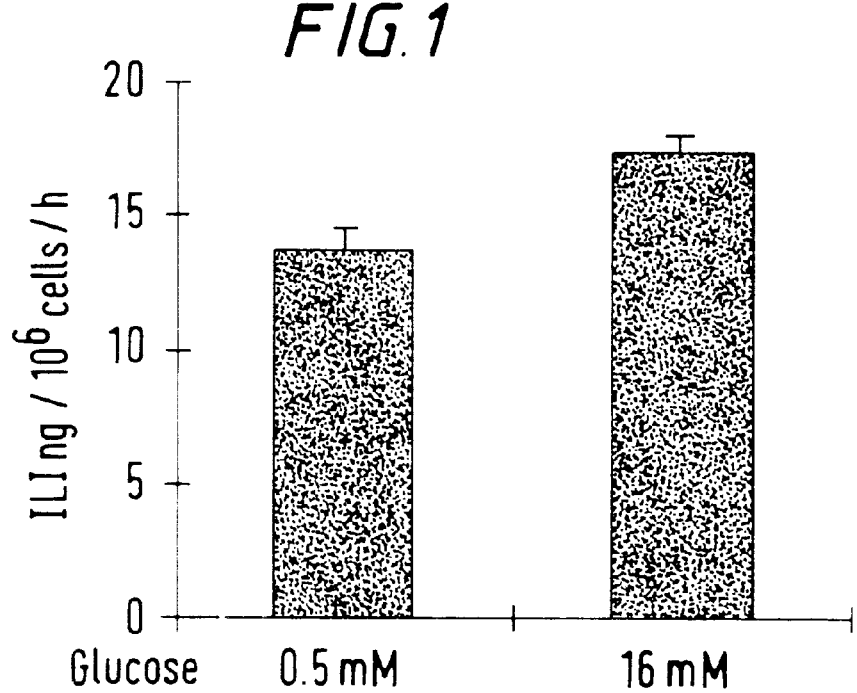

RIA of insulin release from NES 2Y-derived cell lines.

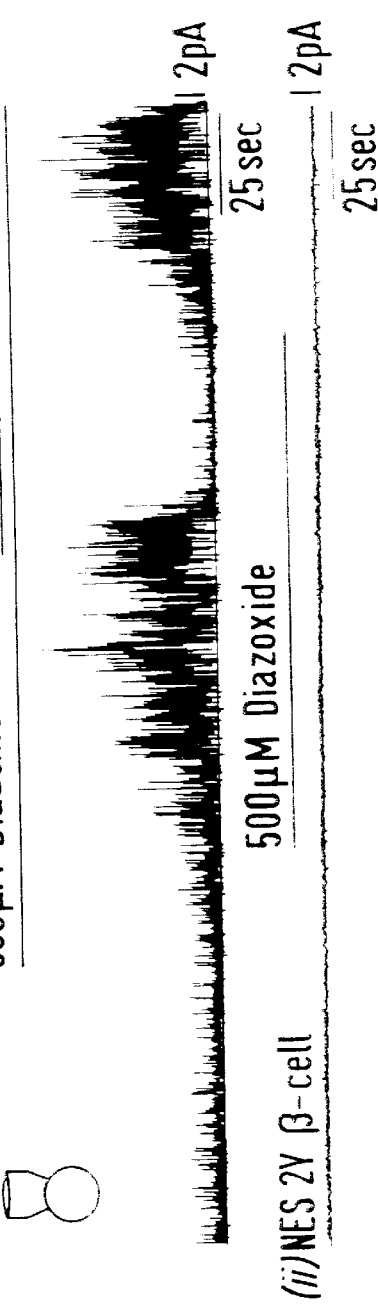
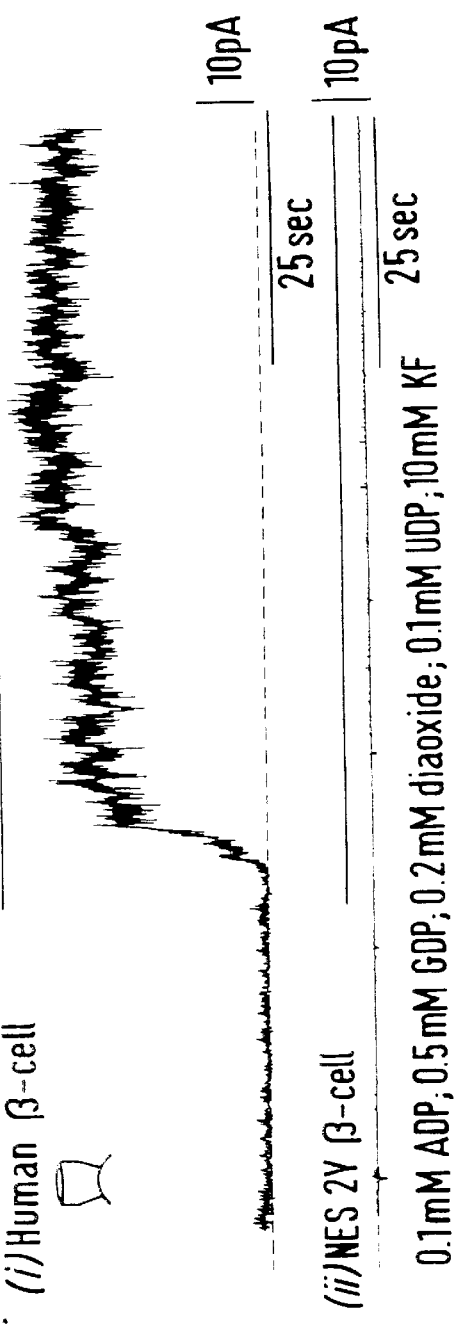
FIG. 9A.
FIG. 9B.

A = NES 2Y RNA  B = NISK9 RNA

FIG. 14 A.
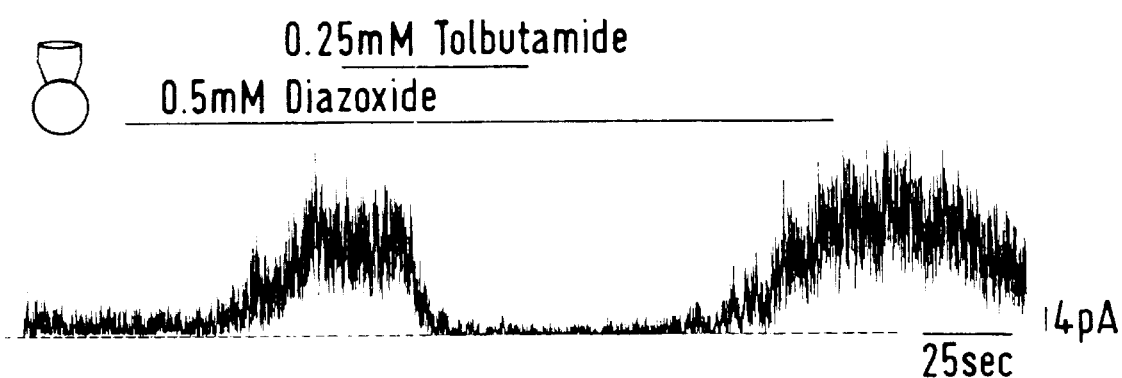
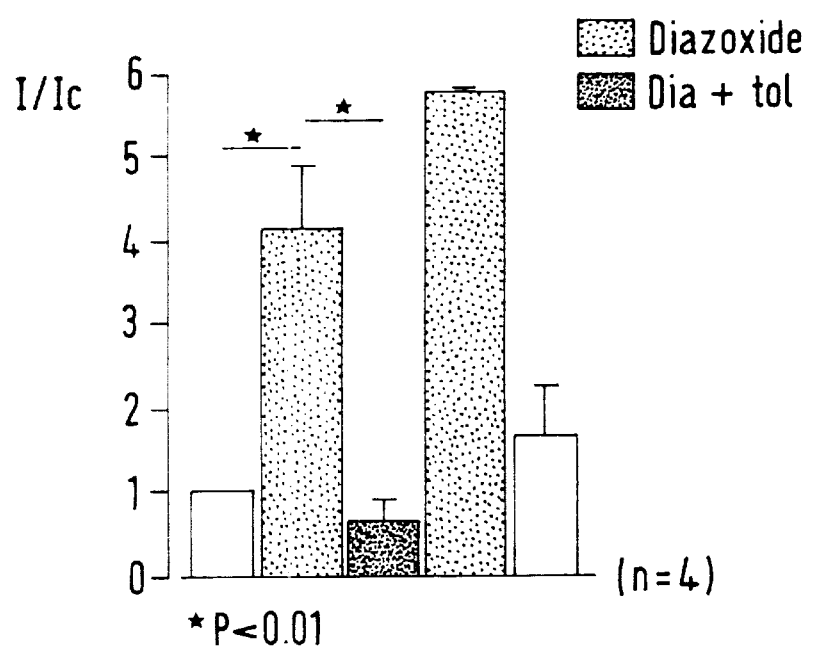

FIG. 14 B.
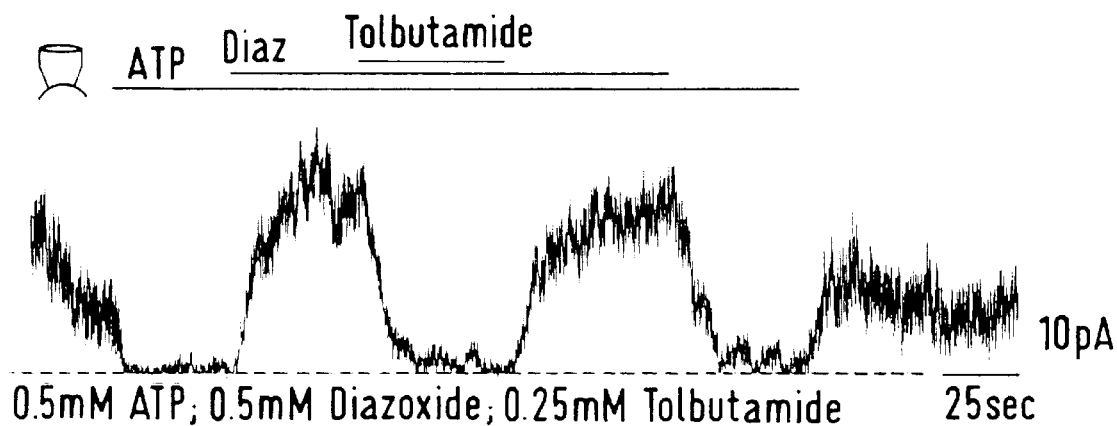
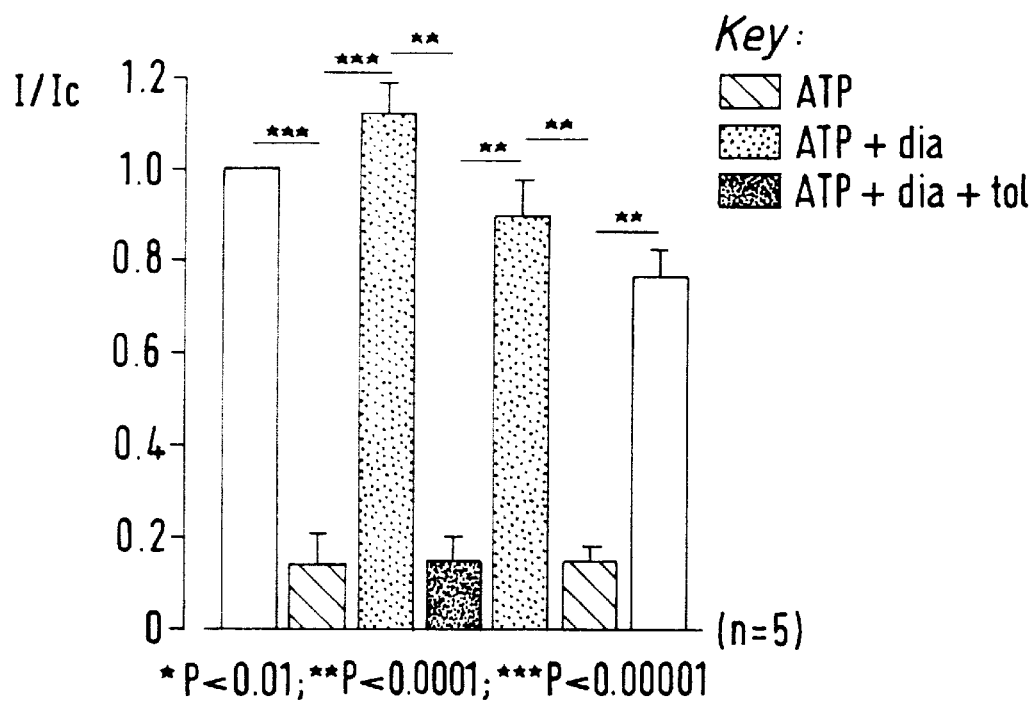

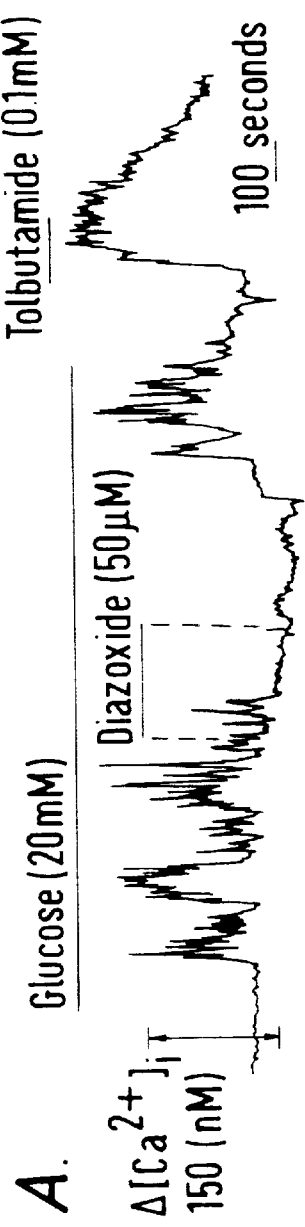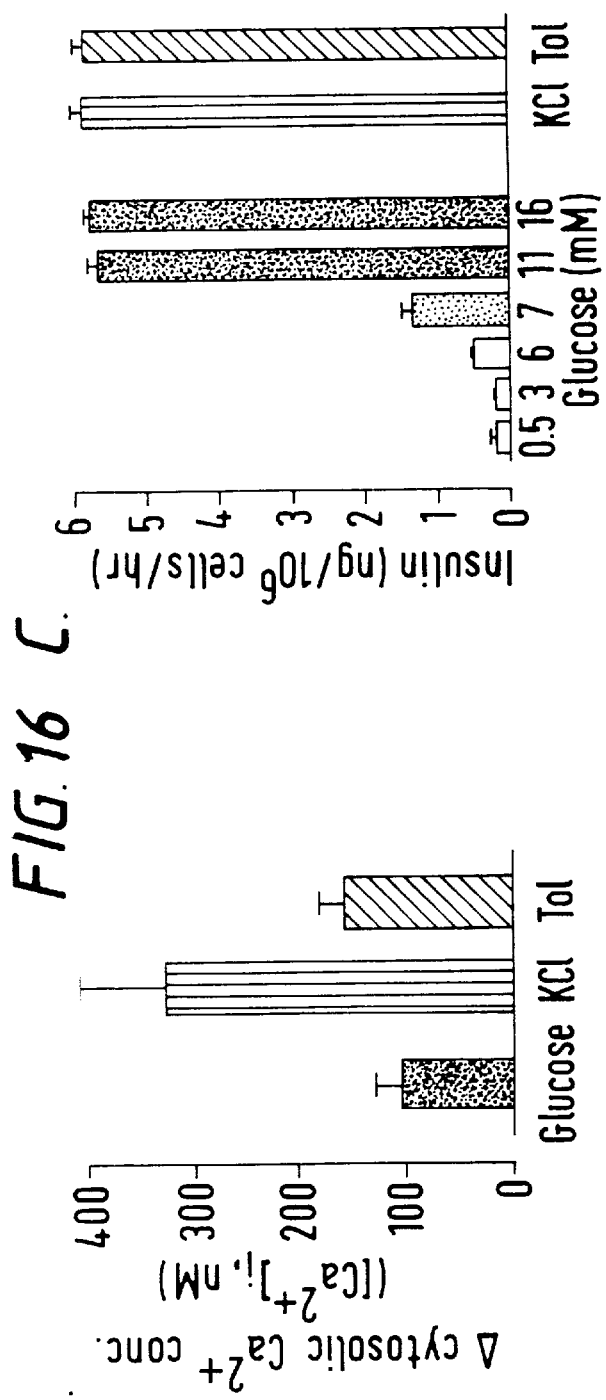
FIG. 16 A.
FIG. 16 B.
FIG. 16 C.

GLUCOSE RESPONSIVE BETA-CELL LINE

The present invention relates to an immortalized glucose responsive β-cell line. Such cell lines are particularly useful in the treatment of type 1 diabetes in humans but insulin control in other mammals is envisaged as well as cross species Production and use.

In type 1 (insulin dependant) diabetes mellitus the principal defect is the destruction of pancreatic β-cells with the resultant loss of insulin production. The condition is normally controlled by the administration of insulin. However, presently available procedures for insulin delivery do not reinstate the normal regulation of glucose metabolism. In non-diabetic people the secretion of insulin is characterised by a basal secretion which occurs between meals and during the night, and secretion that is stimulated in response to a meal. Commercial preparation of fast-acting (NRI-HI) and slow-acting (ultralente) insulins fail to mimic these natural patterns of secretion in diabetic patients. The fastest acting insulin preparations have a slower onset and more prolonged effect than stimulated insulin secretion, while slow acting insulins produce levels of insulin elevated far above those seen during basal secretion. The net result is that patients on subcutaneous insulin injections have a great difficulty in controlling their glycaemia without risk of significant hyperglycaemia, hypoglycaemia or hyperinsulinaemia. The results of the Diabetes Control and Complication Trial (DCCT) have shown that stringent glycaemic control can significantly reduce the appearance of long-term complications such as nephropathy, retinopathy, neuropathy and cardiovascular disease. Hypoglycaemia is unacceptable and dangerous, while hyperinsulinaemia is associated with a higher risk of atherosclerosis. This is discussed in a background paper, Clinical Science (1997) 92,321–330.

It has thus been clear for many years that there is a requirement for the development of new approaches to improving glycaemic control in diabetic patients. In combination with improved methods for self-monitoring of blood glucose concentrations, open-loop and closed-loop continuous insulin infusion devices have been developed to provide near-normal glycaemia. However, the use of these devices is compromised because: a) some are inappropriate for ambulatory patients; b) they are not fail-safe; c) they do not provide a lophysiological replacement of normal amounts of insulin; and d) they necessitate a high degree of motivation and extensive training on the part of the patient.

The ideal treatment for type I diabetes would be the replacement of the patient's destroyed β-cells with transplanted pancreatic Islets of Langerhans. However this approach has two major drawbacks: a) the patients have to be treated with immunosuppressants to prevent rejection of the transplanted islets; and b) it is dependent on the availability of tissue from human cadavers. In addition the ability to prepare pure islets from such donor tissue has proved problematic. Porcine Islets have been suggested as a convenient alternative. However, problems have arisen as a result of the purity of porcine Islet preparations, tissue availability, storage, and transplant rejection.

An alternative approach to treatment, which might improve the control of circulating glucose concentrations, is the implantation of cells which have been genetically modified in vitro to express insulin. Accordingly, cultured cell lines might be manipulated to express insulin by DNA-mediated gene transfer, and the cells encapsulated and implanted into the patient. Several approaches have been adopted:

1) Engineering β-cell lines: a number of rodent or hamster β-cell lines are in use. These have been generated by X-ray irradiation of isolated Islets of Langerhans, transformation of isolated Islets of Langerhans by DNA tumour viruses, expression of the SV40 large T antigen in β-cells of transgenic mice or by cell fusion of Islets of Langerhans with immortalized cell lines. The problem with these cell lines is that they tend to dedifferentiate after a period of time in continuous culture. This results in a loss of glucose sensitive insulin secretion from the physiological range (4–10 mM) to a sub millimolar range. Also, because these cells are highly proliferative it is difficult to predict (based on animal studies) the levels of insulin secreted when implanted into diabetic patients i.e. as the cells proliferate within the animals the insulin levels become too high and the animals become hypoglycaemic.

2) Engineering non-β neuroendocrine cells. Cells such as the mouse corticotrophic cell line AtT20 can be stably transfected with insulin. However, although these AtT20ins cells efficiently process proinsulin to insulin, they do not secrete insulin in response to glucose. Attempts to make AtT20ins cells glucose responsive by transfecting with the glucose transporter GLUT-2 (to generate AtT20insGLUT-2 cells) have been unsuccessful—the cells show some response to glucose but in the sub-physiological range. A major problem with the use of neuroendocrine cells is that endogenous neuropeptides or hormones (e.g. ACTH) that are co-secreted with insulin may antagonise the effects of insulin or otherwise upset the metabolic balance of the patient. Thus we have shown that although some degree of glycaemic control can be achieved by implanting AtT20ins or AtT20insGLUT-2 cells in diabetic animals, after a period of time hyperglycaemia occurs because the animals have become insulin resistant as a consequence of the elevated ACTH levels secreted by the implanted cells.

3) Engineering non-neuroendocrine cells. Muscle, liver and fibroblast cells have been used to administer insulin. The problem with these cells is they do not have the capacity to process proinsulin to insulin or to sense changes in circulating glucose levels. The first problem has been overcome by mutating the proinsulin cleavage sites to the recognition sequence for the ubiquitously expressed protease furin. The second problem regarding engineering glucose sensitive insulin secretion in non-neuroendocrine cells may be beyond the scope of present technologies and knowledge. However, a constitutive trickle release of insulin from these cells may have therapeutic value under certain circumstances.

4) The final approach is to engineer primary cells taken from diabetic patients. These cells would be of non-neuroendocrine origin, i.e. muscle or fibroblast. The aim would be to attain a stable trickle release of insulin using the mutant proinsulin molecule engineered for cleavage by furin.

Despite progress in the above areas no-one to date has engineered or cloned a cell line which grows well in culture and which secretes insulin in response to changes in glucose concentration in the physiological range. Such a human pancreatic β-cell line has long been sought. We have now succeeded in generating a number of such cell lines using a novel approach based on engineered β-like cells inter alia isolated from patients with persistent hyperinsulinaemic hypoglycaemia of infancy PHHI (also known as nesidioblastosis, nesidioplasia of the pancreas, persistent neonatal hyperinsulinism, congenital hyperinsulinism, familial hyperinsulinism (with hypoglycaemia), persistent infantile hyperinsulinism, hyperinsulinaemic hypoglycaemia, microadenomatosis, islet cell hyperplasia, focal hyperinulinism, diffuse hyperinsulism, glucokinase upregulation disorder, glyceraldehyde dehydrogenase disorder, syndrome of hyperinsulinism and hyperammonemia, insulinoma of childhood).

Although we have used cells derived from PHHI, it will be appreciated that immature cells from other sources or bio-engineered cell lines may be used so long as they give rise initially to immortalized unregulated insulin secretion. By the term immortalized is meant a cell line which proliferates in vitro in culture. Islet cells isolated from some patents with PHHI are ideal for producing a cell line because they spontaneously proliferate in vitro.

By cell line we include cell lines derived from cell lines of the present invention and into which cell DNA from the patented cell line has been incorporated.

Persistent hyperinsulinaemic hypoglycaemia of infancy (PHHI), or nesidioblastosis, although a rare disorder characterised by unregulated insulin secretion and profound hypoglycaemia in infancy and childhood, is the most common cause of persistent hypoglycaemia in childhood. PHHI arises from developmental and dysfunctional abnormalities of the pancreatic β-cells. Newly born children with the disease can suffer severe brain damage if not diagnosed and treated immediately. Treatment in severe cases usually involves partial or even total pancreatectomy.

There is controversy over the aetiology of the disease. The term nesidioblastosis (PHHI) was coined in recognition of the histological appearance of endocrine cells lying in duct epithelium with an apparent failure to aggregate into discrete Islets of Langerhans. However, severe hyperinsulinaemia can also occur in the presence of apparently normal Islets, and doubt has been expressed over the concept that the condition is entirely due to a defect in β-cell differentiation. The disease occurs either in families, particularly in the Middle East, or sporadically.

We have accordingly made two discoveries which enable us to produce an insulin secreting cell line from such an immature source and subsequently to repair the deficiency in the cell line by genetic engineering to give a glucose responsive human β-cell line. According therefore to a first aspect of the present invention there is provided an immortalized insulin producing human β-cell line. This cell line is then bio-engineered to be glucose responsive. The cell line may also be cloned or otherwise proliferated subsequently.

This cell line is preferably derived from immature Islets of Langerhans from a foetal or child donor and may be conveniently derived from a patient with PHHI. Subsequently such a cell line may be genetically engineered to induce glucose responsiveness within the physiological range of 4 to 10 mM. One way of producing this is to transfect the insulin producing cloned human β-cell line with the homeodomain factor PDXI (also referred to as $IUF_1$) and subsequently stably co-transfecting the resultant product with cDNA encoding SUR1 and optionally Kir 6.2 (components of the $K_{ATP}$ channel). The resultant products may then be rendered into a form which is implantable e.g. may be encapsulated, or used for screening of novel drug targets for PHHI and other glucose regulation disorders. Specifically the cell line of the invention may be used for at least one of the following:

(a) screening of cationic or anionic selective ion channels;

(b) screening of intracellular and/or cytosolic concentration of calcium ions;

(c) screening of processes for exocytosis or endocytosis of secretary granules;

(d) screening of processes for cell division and/or differentiation;

(e) screening of processes for glucose-induced insulin release via depolarization-response coupling events, or augmentation pathways;

(f) screening of processes for glucose-induced insulin gene transcription or gene transcription associated with diabetes PHHI or insulinomas;

(g) screening of processes for elucidation of β-cell specific ion channels or receptors therefor; and (h) screening of processes for elucidation of the pharmacology of ion channel modulation proteins.

In a further aspect of the invention there is provided a method for the production of an immortalized glucose responsive insulin producing human β-cell line which comprises selecting an unregulated immortalized human insulin secreting β-cell line, transfecting said selected cell line with elements for the genetic control of glucose responsiveness and proliferating the transfected cell line. Such cells may be subjected to the further steps of genetically engineering the resultant cell line to be glucose, responsive within the physiological range by transfecting with a cDNA encoding PDX1 and subsequently stably co-transfecting the resultant product with cDNA encoding both SUR 1 and Kir 6.2 to form an NISK 9 cell line.

The NISK 9 cell line so produced has been deposited under the provisions of the Budapest Treaty under No. 9709106 at The European Collection of Cell Cultures; Centre for Applied Microbiology and Research, Salisbury, Wiltshire, United Kingdom on Sep. 1, 1997.

The NES2Y cell line is deposited under No. 98081006 at the European Collection of Cell Cultures; Centre for Applied Microbiology and Research, Salisbury, Wiltshire, United Kingdom on Sep. 14, 1998.

According to other embodiments of the present invention there are provided methods of treatment of the human body with PHHI, methods for the treatment of the human body with diabetes, and a method for the treatment of the human body with a condition resulting from abnormal insulin secretion. In this respect, the method of treatment may comprise producing in vitro an immortalized insulin producing human β-cell line which is glucose responsive and thereafter implanting the cells from the cell line into the human body.

Conveniently the cell line is derived from immature, that is to say foetal or a younger child, Islets of Langerhans. Preferably the immature Islets of Langerhans are from the body to which treatment is to be effected. If the immature Islets of Langerhans are taken from the same body as they are implanted into there is a reduced likelihood that they will be rejected.

In a preferred embodiment the Islets of Langerhans are from a foetus or a child with PHHI. Such Islets of Langerhans produce a cell line which is immortal and stable.

Alternatively, the cell line may be derived from a cell-line bio-engineered to produce unregulated insulin secretions.

Preferably the cell line is genetically engineered to be glucose responsive within the physiological range of 4 to 10 mM. One method of producing such a responsive cell line is to transfect the cells with cDNA PXD1 and then to co-transfect cDNA encoding SUR1 and optionally Kir 6.2.

The invention will now be described by way of illustration only with reference to the accompanying figures and subsequent examples of the invention.

FIG. 1: Effect of glucose on insulin secretion from NES 2Y cells. NES 2Y is the name of the cell line derived from the patient with PHHI.

NES 2Y cells were preincubated from 180 min in media containing 0.5 mM glucose. The media was then replaced with that containing the indicated amount of glucose and the media samples assayed for insulin by radioimmunoassay after a further 60 min incubation. The data are representative of two experiments and show the mean ± standard deviation of 6 separate determinations. The data shows that NES 2Y cells secrete high amounts of insulin and secretion is responsive to glucose levels.

Figure 2:
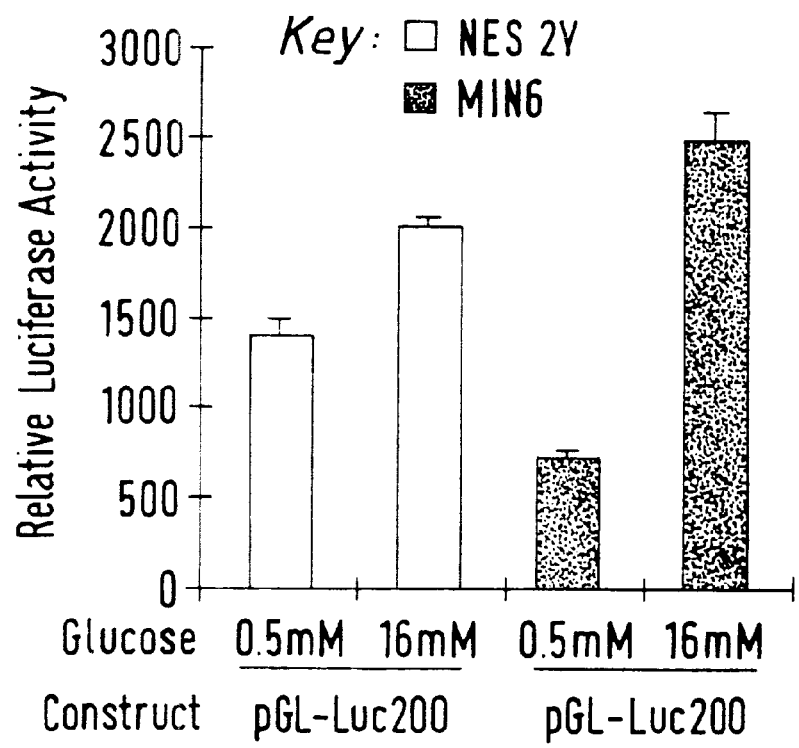

FIG. 2: Effect of glucose on pGL-LUC200 constructs in transfected MIN6 and NES 2Y cells.

NES 2Y cells or MIN6 cells were transfected with pGL-LUC200, in which firefly luciferase is driven by a −50 to −250 bp fragment of the human insulin gene. After 24 hours cells were reincubated for 3 hours in 0.5 mM glucose and then incubated in low (0.5 mM) or high (16 mM) glucose for 24 hours. Values are shown as relative luciferase activity standardised against protein content. The data are representative of two separate experiments and show the mean ± standard deviation for 4 separate determinations. The data show that the LUC200 construct is responsive to glucose in the MIN6 cell line but unresponsive to the NES 2Y cell line.

Figure 3:
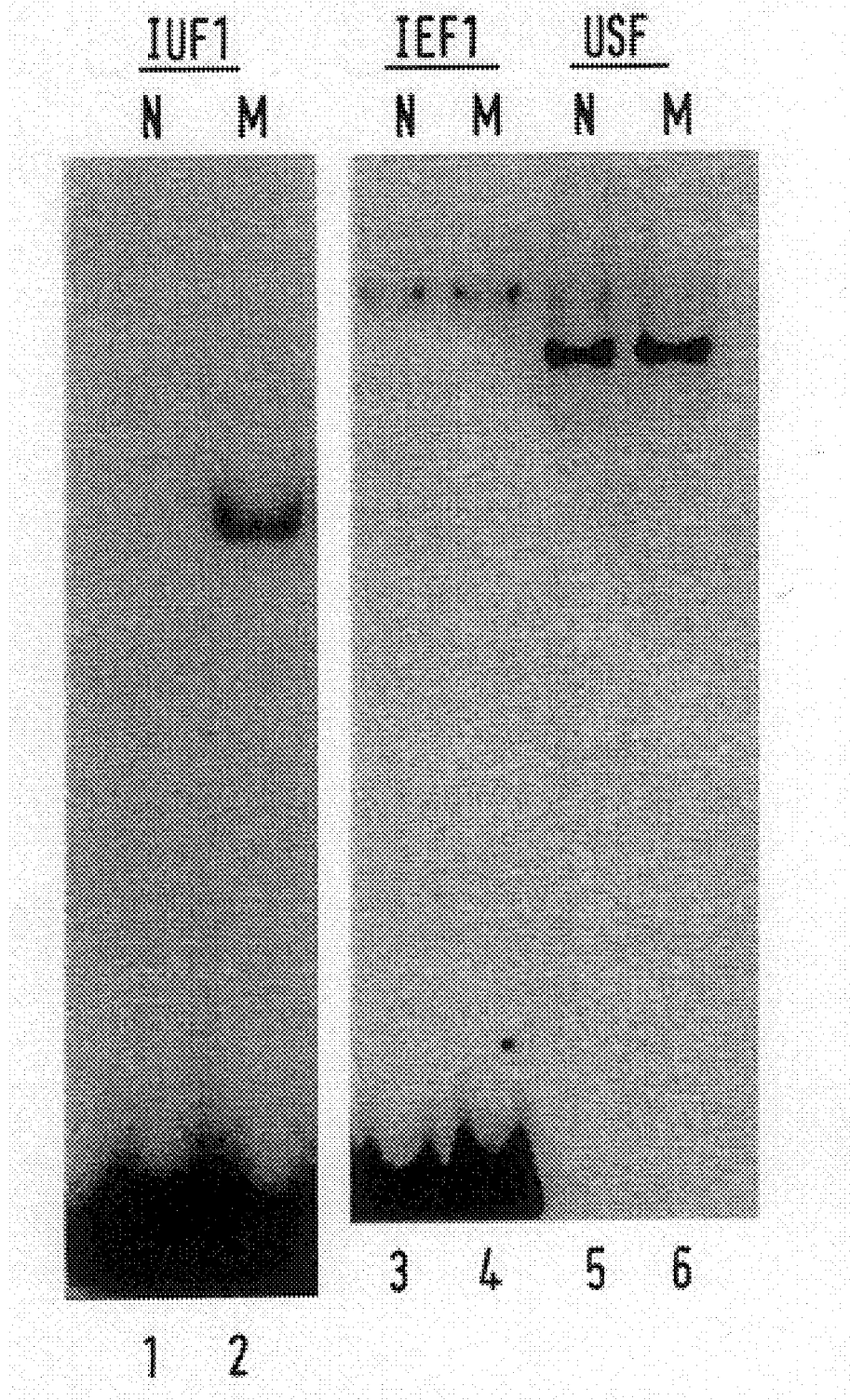

FIG. 3: EMSA (Electrophoretic Mobility Shift Assay) analysis of transcription factor binding activity in NES 2Y (N) and MIN (M) cells.

NES 2Y and MIN6 cells were incubated for 1 h in 16 mM glucose and analysed by EMSA for the binding activities of IUFL using (oligonucleotide B [13], lanes 1 and 2), USF (oligonucleotide USF [20] lanes 5 and 6), and IEF1 using oligonucleotide Jr1 [20], lanes 3 and 4. IUF1 DNA binding activity is undetectable in NES 2Y cells.

Figure 4:
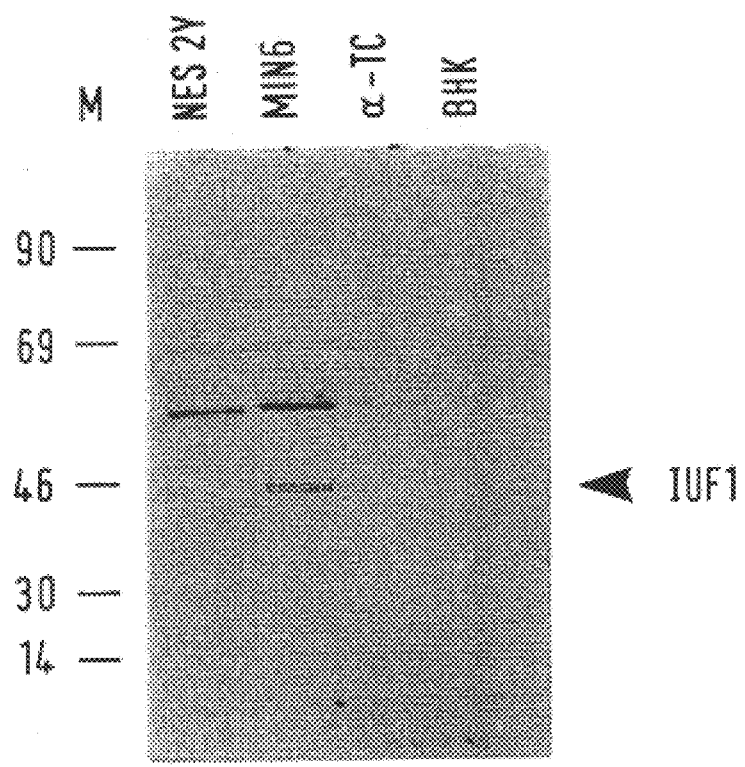

FIG. 4: Western blot analysis of IUF1 in NES 2Y, MIN6, Ai TC and BHK cells.

The indicated cell lines were analysed for the IUF1 protein using a specific IUF1 antibody. The arrow indicates IUF1, which has a molecular weight of 46 kDa. The higher molecular weight band in tracks 2 and 3 is observed in all β-cells and does not represent IUF1. Lane 1 contains rainbow molecular size markers. IUF1 cannot be detected by western blotting in NES 2Y cells.

FIG. 5: Quantitative RT-PCR of IUF1, insulin and USF mRNA levels.

Comparison of quantitative PCR with primers specific for IUF1 (NES 2Y, lanes 1–6, MIN6, lanes 7–12) insulin, and USF. Lanes 1–6 and 7–12 represent 10%, 5%, 2.5%, 1%, 0.1% and 0.01% of total cDNA as template respectively. M indicates Kilobase size markers. The amplified IUF1 fragment has an expected size of 850 base-pairs, USF 900 base-pairs, and insulin 350 base-pairs. IUF1 mRNA can be detected in NES 2Y cells but only at very low levels. Thus PHHI is associated with the impaired expression of IUF1.

Figure 6:
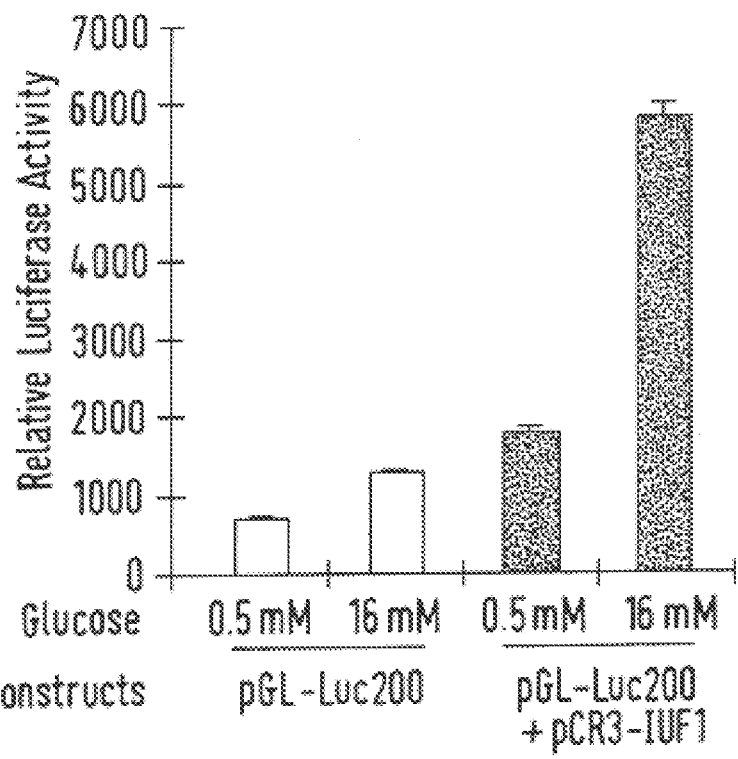

FIG. 6: IUF1 restores glucose responsive regulation of the insulin promoter in transfected NES 2Y cells.

NES 2Y cells were transfected with pGL-LUC200, or co-transfected with pGL-LUC200 and pCR3-IUF1, as indicated. Cells were then incubated in 0.5 mM glucose or 16 mM glucose for 24 h. Values are shown as relative luciferase activity standardised against protein content. Data are representative of two experiments and show the mean ± S.D. of four separate determinations. The defect in glucose responsive control of insulin gene transcription can be repaired by stably transfecting the NES 2Y cells with IUF1. See also claim 11 hereinafter.

Figure 7:
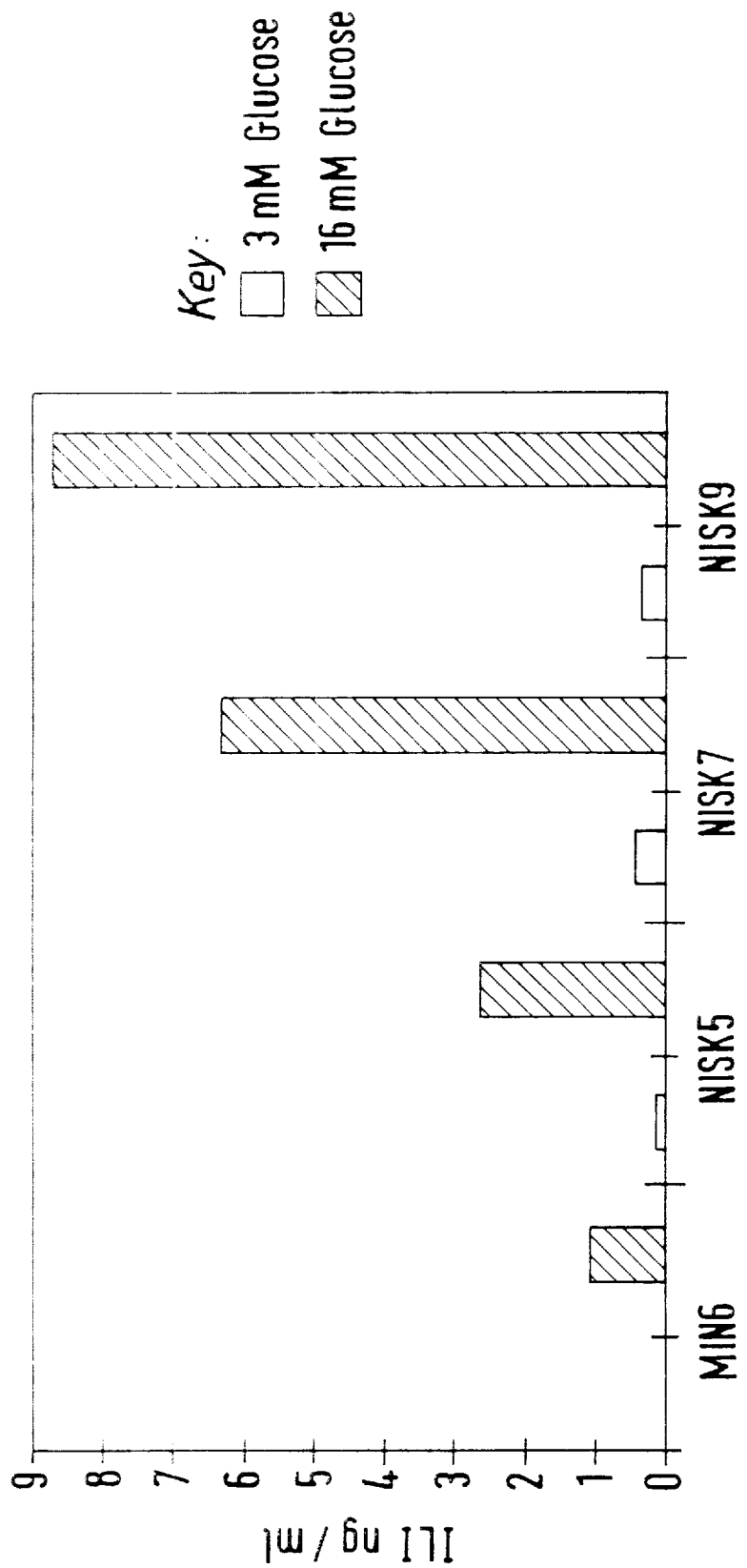

FIG. 7: Effects of Glucose on insulin secretion from NES 2Y-derived NISK clones.

NES 2Y cells were stably transfected with IUF1, Sur1 and Kir 6.2, to generate NISK clones. Clones NISK5, NISK7 and NISK9, along with the parent NES 2Y cells were preincubated for 180 minutes in media containing 0.5 mM glucose. The media was then replaced with that containing 16 mM glucose, and the media samples assayed for insulin by radioimmunoassay after a further 60 minutes incubation. The three NISK cell lines were selected on the basis of their insulin secretory response to glucose in the physiological range.

Figure 8:
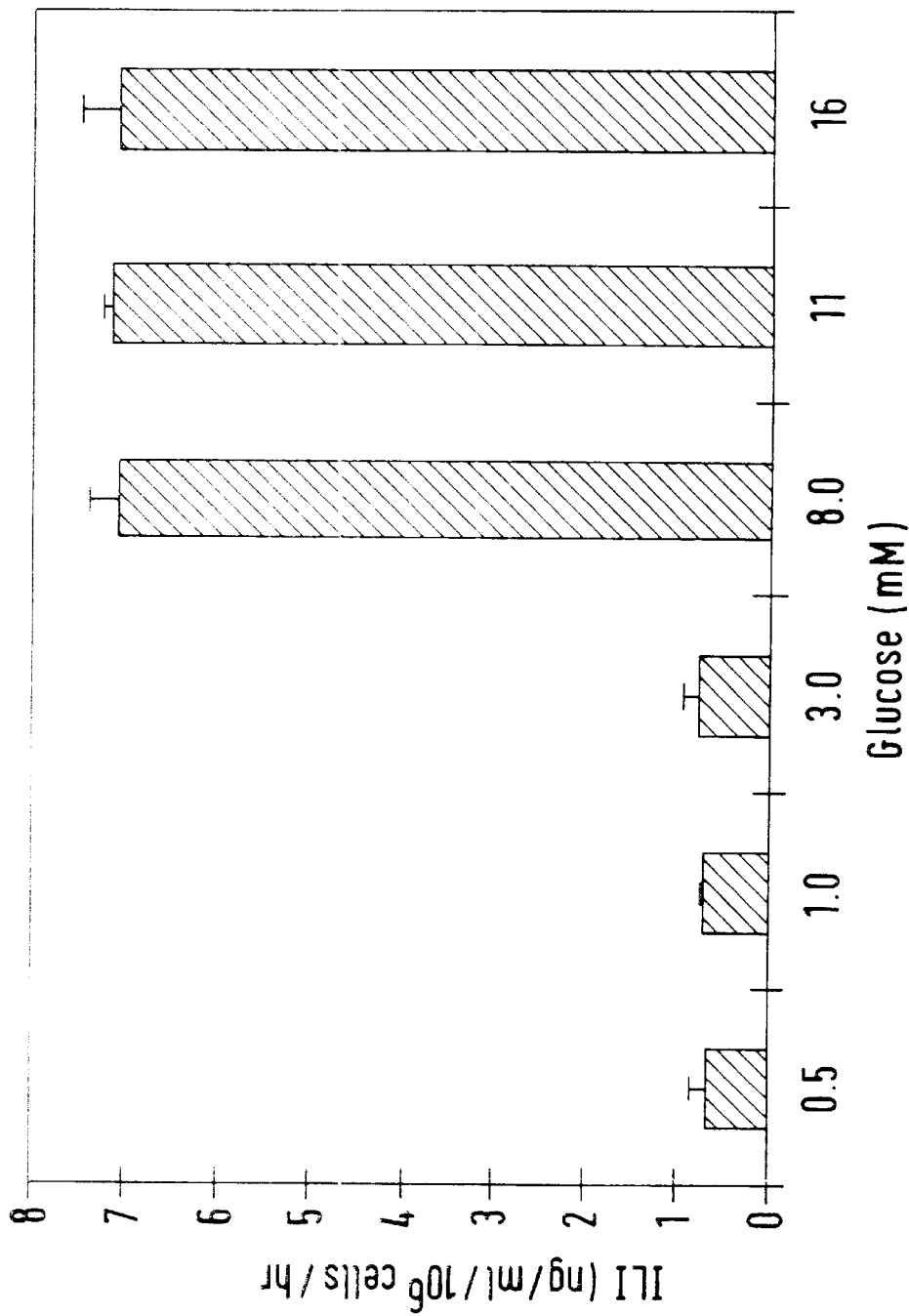

FIG. 8. Shows the dose-response of NISK9 cells to glucose.

NISK 9 cells (NES 2Y cells stably transfected with IUF1, Sur1 and Kir 6.2) were preincubated for 180 minutes in media containing 0.5 mM glucose. The media was then replaced with that containing the indicated concentrations of glucose, and the media samples assayed for insulin by radioimmunoassay after a further 60 minutes incubation. The data are presentative of two experiments, and show the mean +/− standard deviation of 6 separate determinations. The NISK9 cell line is shown to secrete insulin in response to changes in glucose in the physiological concentration range.

FIG. 9: The absence of $K_{ATP}$ channel activity in NES 2Y β-cells.

All data obtained using the patch-clamp technique in the cell attached configuration, panel A, or the "cell-free" inside-out configuration, panel B. Control data obtained from human β-cells reveals that spontaneously open $K_{ATP}$ channels are activated by diazoxide (500 $\mu$M) and inhibited by the sulphonylurea tolbutamide (200 $\mu$M) panel A. In panel B, a "cocktail" of nucleotides, potassium fluoride (KF) and diazoxide added directly to the internal face of the membrane are shown to cause a marked increase in $K_{ATP}$ channel activity. (In the record shown, the maximum number of coincident open ion channel events is increased from 3 to 30). Under the same experimental conditions none of these agents had any action on ion channel events in the NES 2Y β-cells. Similar data were obtained in 4 (panel A) and 18 (panel B) other control experiments, and in a total of N=10 (panel A) and n=10 (panel B) NES 2Y β-cells experiments. Note that upward deflections represent outward current events, and that the broken lines indicate the zero current level which corresponds to closure of all $K^+$ channels. The same ionic gradients were used for each of the experimental protocols described, and all data are plotted to the same scales in each panel.

Figure 10:
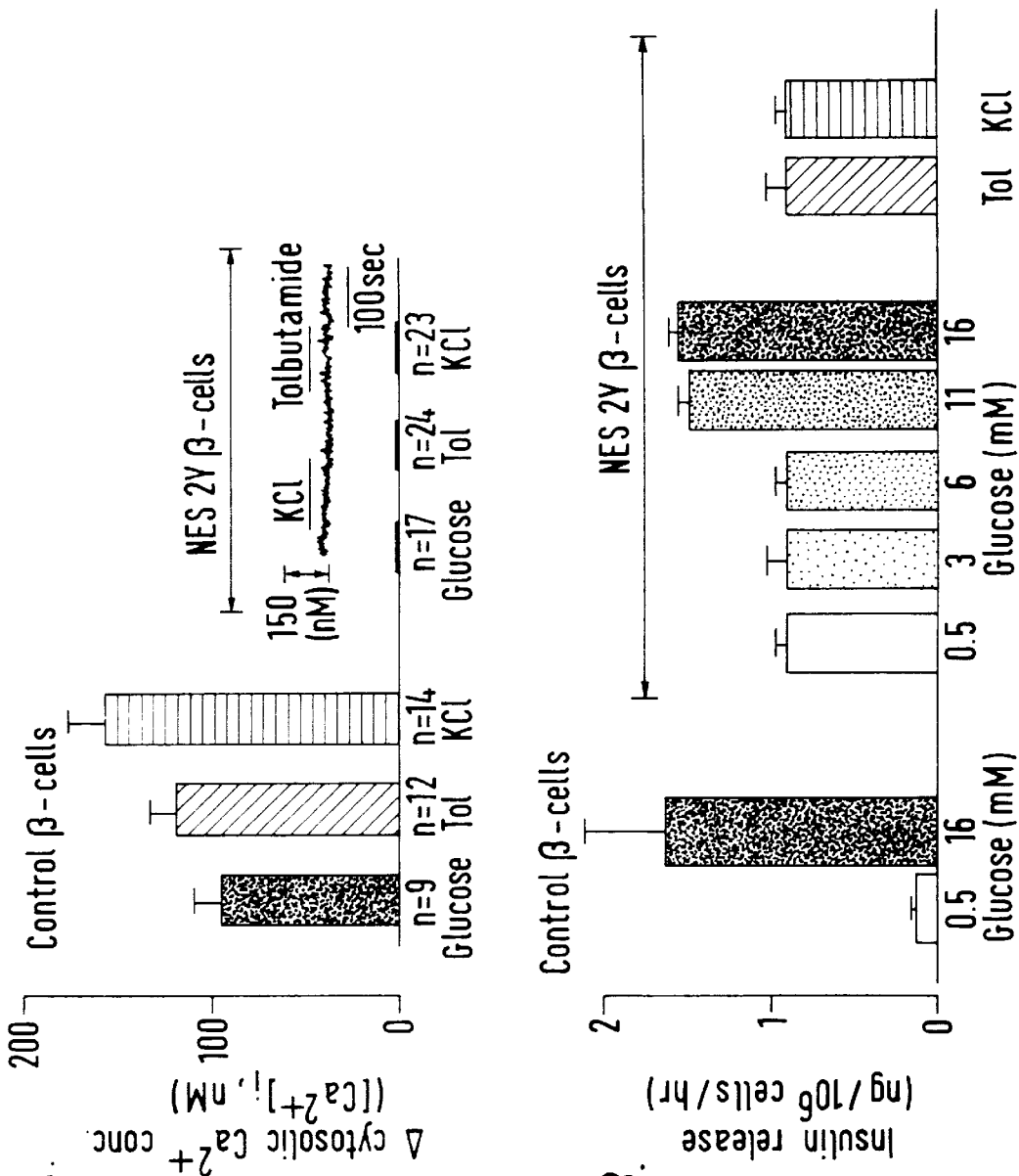

FIG. 10: NES 2Y β-cell function.

Panel A illustrates that the regulation of cytosolic $Ca^{2+}$ ($[Ca^{2+}]_i$) signalling in NES 2Y β-cells is severely compromised, since in comparison to control data (obtained from mouse islets) there was no elevation of $[Ca^{2+}]_i$ when the cells were challenged with KCl (40 mM, n=23), tolbutamide (0.2 mM, n=24) or glucose (20 mM, n=17). A representative experiment and average data obtained from several experiments with NES 2Y β-cells are shown. Panel B illustrates insulin release data obtained from control (MIN 6 β-cells) and NES 2Y β-cells. Note how the NES 2Y β-cells have high constitutive rates of insulin release in the absence of stimuli in comparison to control tissue, that NES 2Y β-cells are poorly glucose responsive and that they fail to release insulin when challenged with 40 mM KCl or 0.2 mM tolbutamide. See also claim 11 hereinafter.

Figure 11:
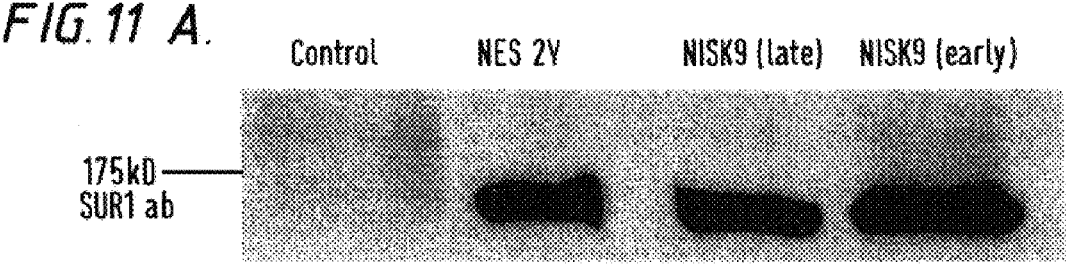
Figure 11:
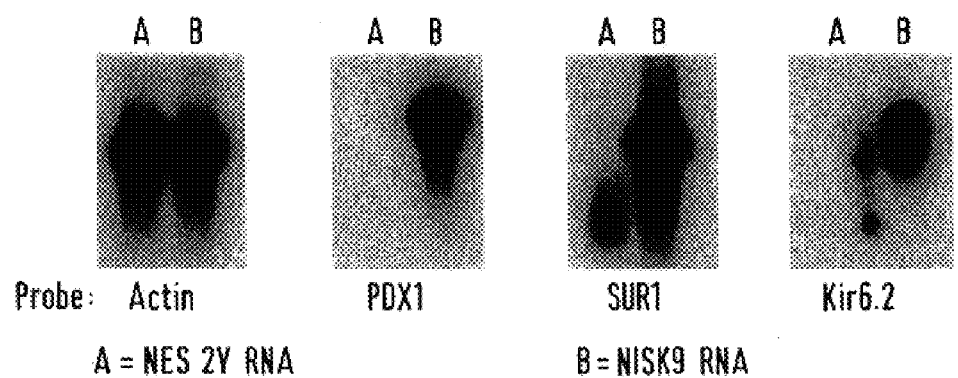

FIG. 11: Panel A shows Western immunoblotting data using a SUR1 antibody in control (BRIN BD11 cells, lane 1) NES 2Y β-cells (lane 2) and NISK 9 β-cells (lane 3) Note the appearance of a higher molecular weight species (175 kDal): in both control and the transfected cells. This is consistent with glycosylation of the recombinant channel complex. The data shown is representative of two further experiments.

Panel B is a Northern Blot analysis of IUF1, SUR1 and Kir6.2 in Nes2Y and Nisk9 cells. Total RNA was prepared from NES 2Y (A) and NISK (B) cells, separated on a 1.5% agarose/formaldehyde gel, and transferred to Hybond-N+ nitrocellulose membrane. The filter was probed with $^{32}$P-labelled cDNAs encoding actin (as a control), IUF1 (PDX1), SUR1 and Kir6.2. The results show that all three transgenes are expressed in the Nisk9 cells. SUR1 mRNA is larger in Nisk9 compared to the endogenous mRNA in Nes2Y cells because it is expressed from a bicstronic vector mRNA (IRES vector).

Figure 12:
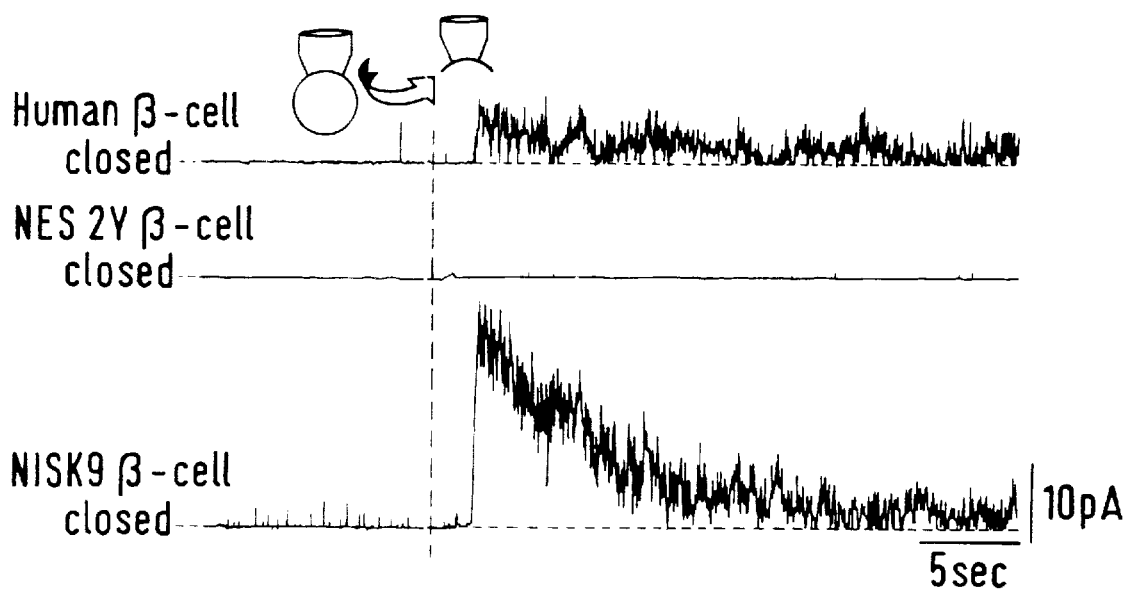
Figure 12:
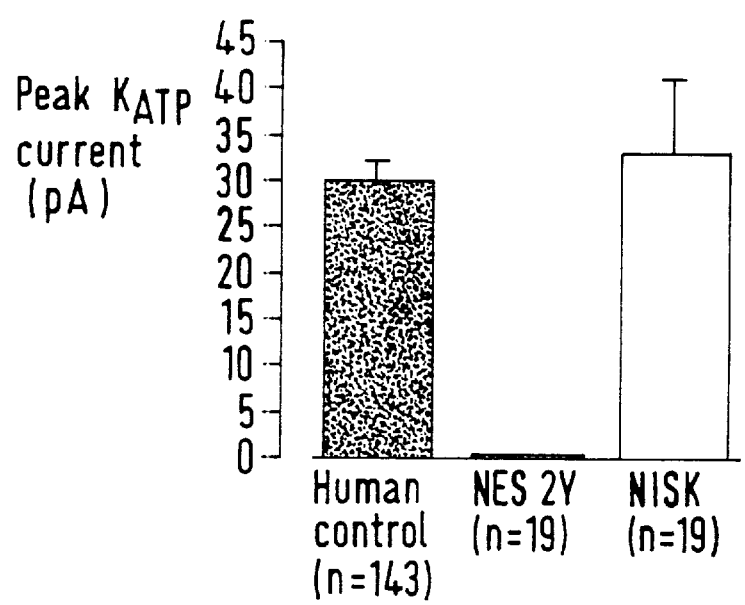

FIG. 12: The appearance of K+ channels in transfected NES 2Y β-cells.

Panel A shows data obtained from human β-cells, NES 2Y β-cells and NISK 9 β-cells under exactly the same experimental conditions. Using a procedure whereby patches of cell membrane are isolated from the intact cell, the appearance of $K_{ATP}$ channels can be "assayed" following wash-out of intracellular ATP. In both control and NISK β-cells there is a marked increase in the $K_{ATP}$ channel associated current upon patch liberation and although there is some patch-to-patch variation in the number of operational channels (see panel A), overall the density of $KAT_p$ channels in control and NISK β-cell is very similar, panel B. Note the absence of any operational $K_{ATP}$ channels in NES 2Y β-cells.

Figure 13:
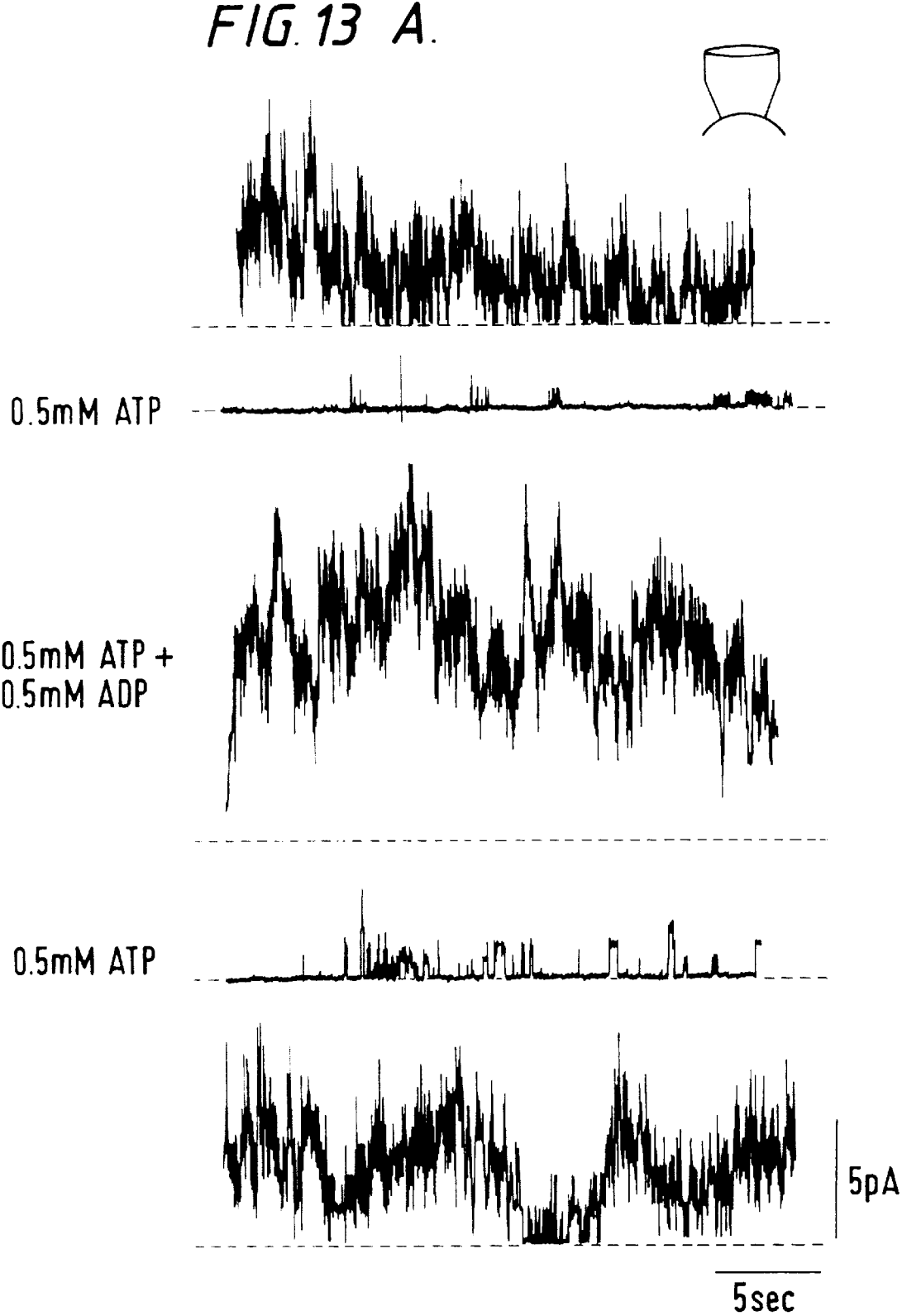
Figure 13:
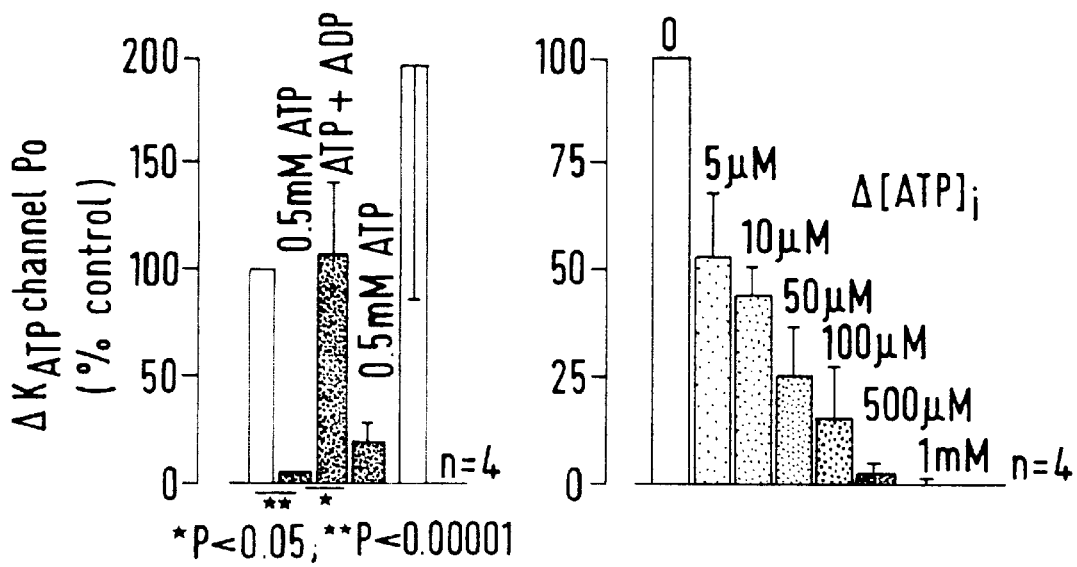
Figure 13:
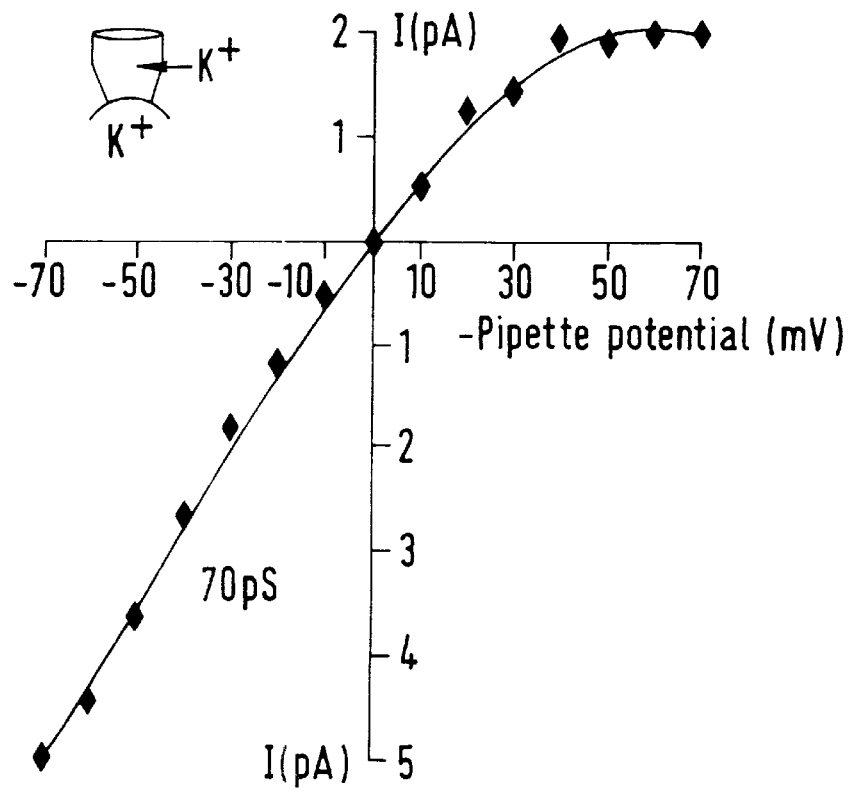

FIG. 13: Properties of recombinant $K_{ATP}$ channels in NISK β-cells.

In panel A, all data come from the same inside-out patch recording. Note the inhibition of channels by ATP, and the subsequent reversible recovery from closure of ADP. (The significance of this data is that changes in the ATP:ADP ratio are causally linked to $K_{ATP}$ channel-dependent changes in the cell membrane potential which underpins glucose-induced insulin release). Similar findings were found in several other patches and analysed for changes in channel open state probability, see panel B. Panel B also shows the average concentration-dependency of inhibition of $K_{ATP}$ channels by elevating concentrations of ATP. Note that 50% inhibition of channels occurs between 5–10 μM ATP, and similar data were obtained in control human β-cell recordings (not shown). Panel C shows a typical current-voltage relationship plot for the recombinant $K_{ATP}$ channel expressed in NISK 9 β-cells. When recorded using symmetrical 140 mM KCl-rich solutions on either side of the cell membrane the channel has an inwardly-retifying relationship, with an estimated inward current conductance of approximately 70 pS. See also claim 11 hereinafter.

FIG. 14: Pharmacological properties of recombinant $K_{ATP}$ channels in NISK 9 β-cells.

Panels A and B were obtained under the same conditions as illustrated in FIG. 9. Both panels show that recombinant $K_{ATP}$ channels are activated by diazoxide and inhibited by tolbutamide (n=4, panel A; n=5 panel B). In panel B, tolbutamide is shown to inhibit diazoxide-activated $K_{ATP}$ channels in an inside-out patch; note that when this configuration is used, ATP must be added to the inside face of the cell membrane to facilitate diazoxide-induced K+ channel activation. Mean data from several experiments are also illustrated in panels A and B. See also claim 11 hereinafter.

Figure 15:
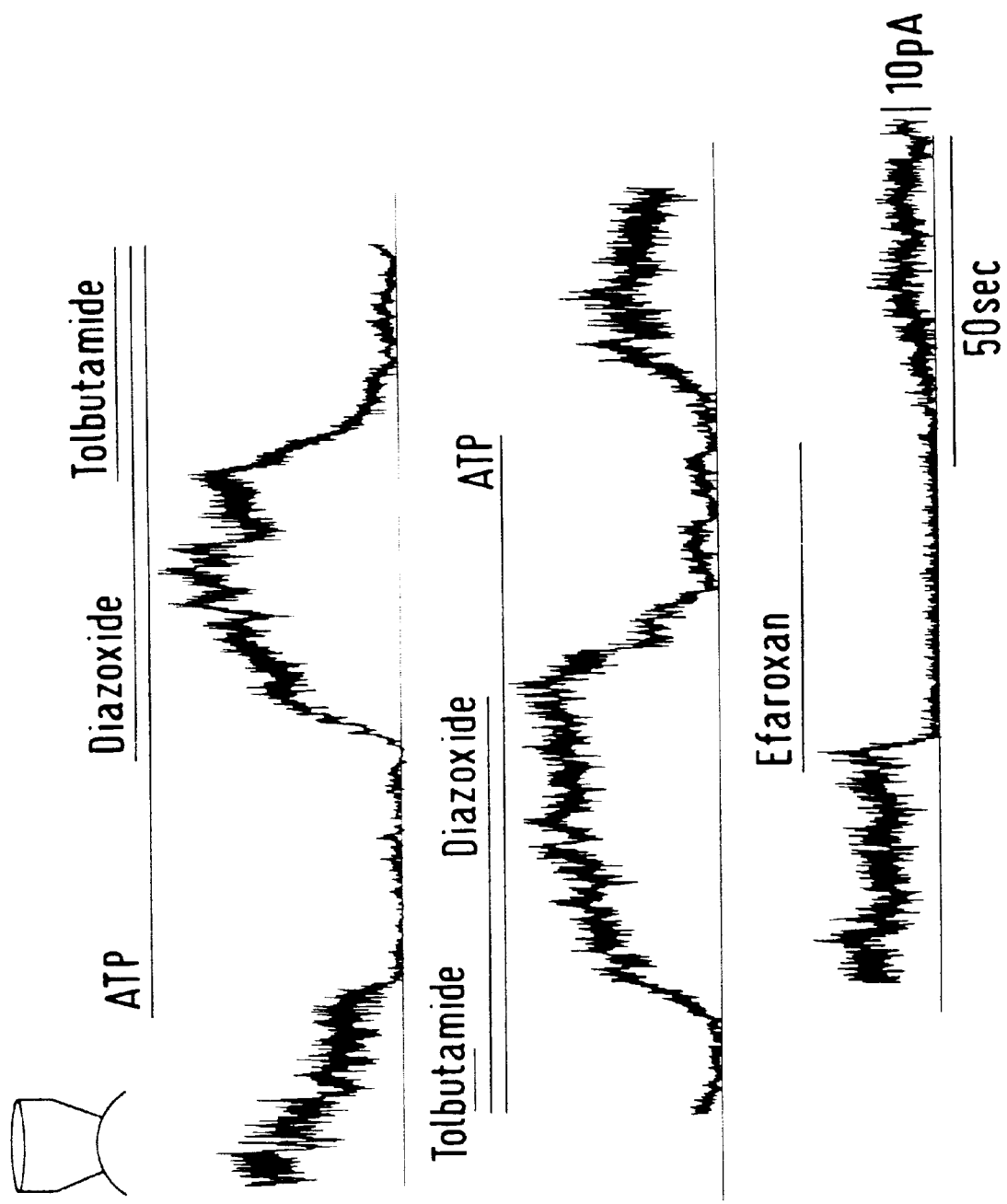

FIG. 15: Pharmacology of engineered $K_{ATP}$ channels in NES 2Y β-cells.

All data comes from the same membrane recording: an inside-out patch record obtained from a NISK 9 β-cell. The data show K' channel block by intracellular addition of ATP (500 μM), activation by diazoxide (500 μM) in the presence of ATP and channel inhibition brought about by both tolbutamide (250 μM) and efaroxan (200 μM). Closure of $K_{ATP}$ channels was also associated with a rise in the cytosolic concentration ($[Ca^{2+}]_1$), not shown. Thus, the $\Delta[Ca^{2+}]_1$ for tolbutamide was found, on average to be 158+/−24 nM (n=22), and for efaroxan 195+/−40 nM (n=12). See also claim 11 hereinafter.

FIG. 16: The functional properties of NISK 9 β-cells.

Panels A and B show that unlike NES 2Y β-cells (see FIG. 10A), NISK 9 β-cells will respond to glucose stimulation through an elevation of the cytosolic $Ca^{2+}$ concentration. The rise in $[Ca^{2+}]_i$ is inhibited by the hyperpolarizing $K_{ATP}$ channel agonist diazoxide (n=5). Like glucose (n=8), both tolbutamide (panels A and B; 100–200 mM, n=22) and KCl (panel B; 40 mM, n=22) also raise $[Ca^{2+}]_i$. On average, the basal $[Ca^{2+}]_i$ levels in NES 2Y and NISK 9 β-cells were found to be 98±7 nM (n=24) and 78±5 nM (n=55), respectively. In panel C, the consequences of $K_{ATP}$ channel operation and the restoration of $Ca^{2+}$ signalling are shown to be linked to the development of regulated insulin secretion in response to glucose (0.5–16 mM), KCl (40 mM) and tolbutamide (0.2 mM). Note how the basal rates of secretion are markedly lower than in the NES 2Y β-cells (see FIG. 10B). Panel C documents that in both control and the transfected cells, glucose causes a marked increase in the rate of insulin gene transcription. See claim 11 hereinafter.

Figure 17:
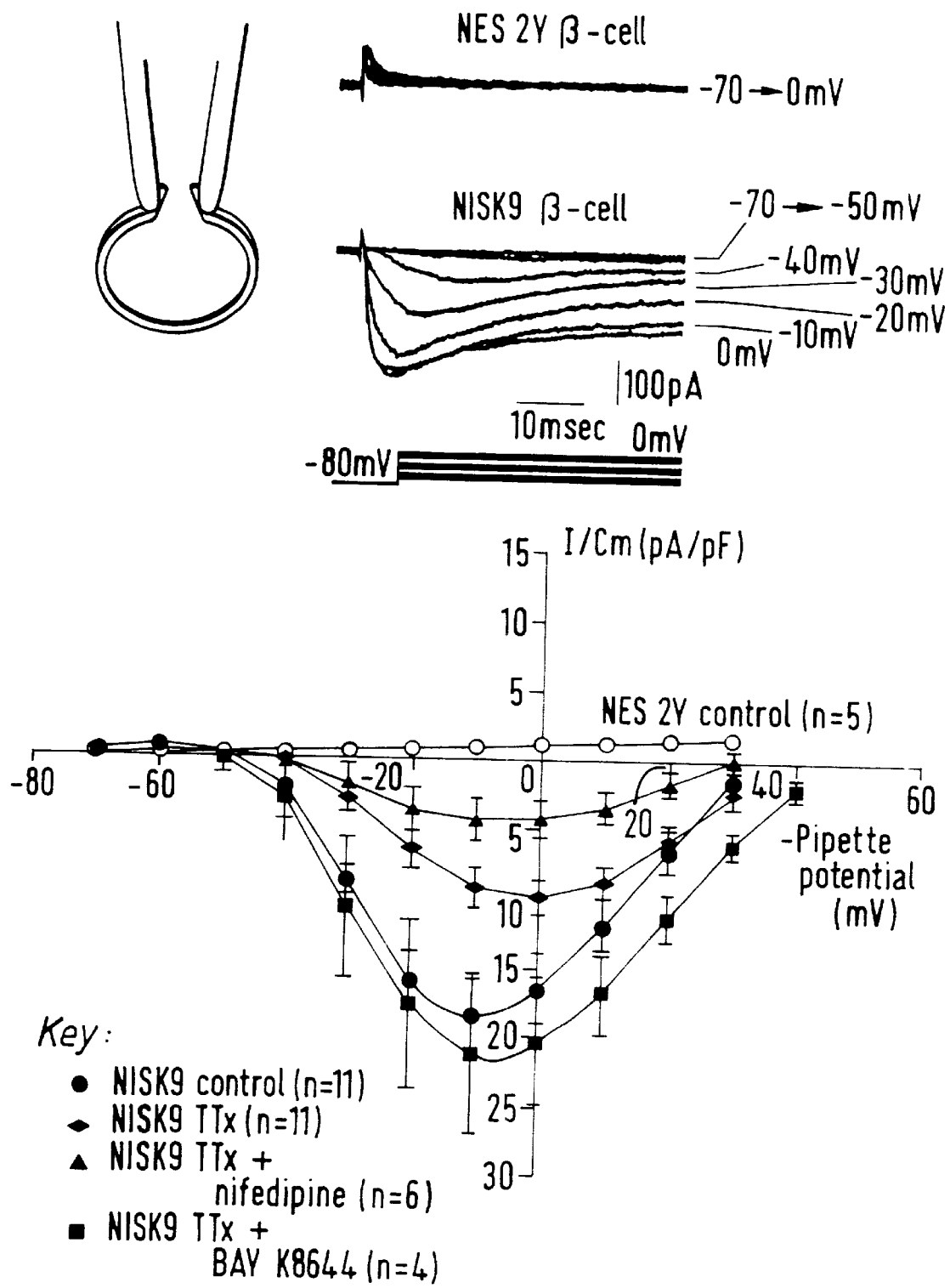
Figure 17:
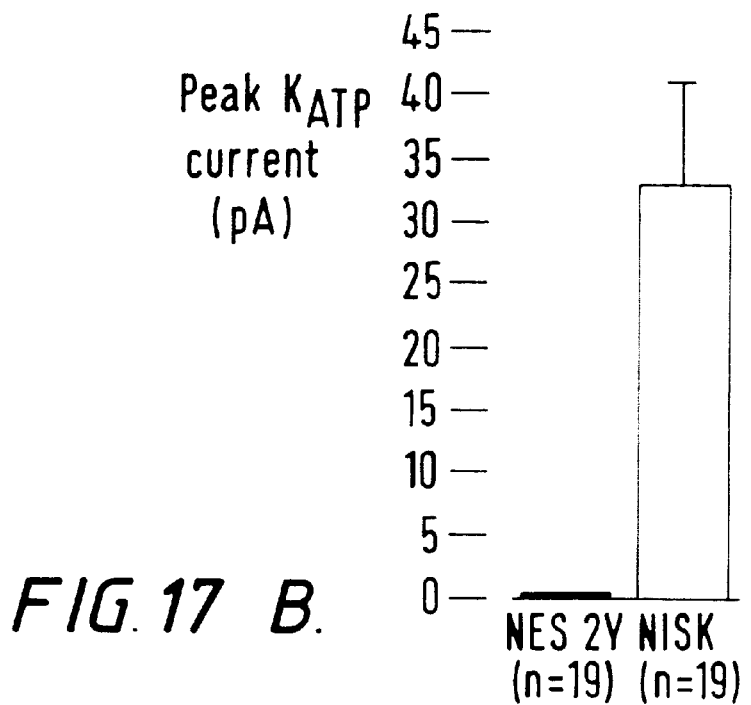

FIG. 17: The absence of voltage-gated ion channels and $K_{ATP}$ channel activity in NES 2Y β-cells.

Data obtained using the whole-cell and inside-out patch variations of the patch-clamp technique. Panel A shows representative voltage-gated currents obtained from the human β-cell lines NES 2Y and NISK 9. Note the absence of any whole cell inward current in the NES 2Y β-cells compared with the NISK 9 β-cells. Panel A also shows a graphical representation of the relationship between the patch-clamp pipette holding potential and the normalised whole-cell current (I=whole-cell current; Cm=cell capacitance) from sEVeral recordings. These data reveal (1) the absence of voltage-gated $Ca^{2+}$ channels and voltage-gated Na+ channels in NES 2Y β-cells (n=5); (2) inhibition of voltage-gated currents by tetrodotoxin (Ttx; 313 nM, n=11), (3) the further inhibition of Ttx-insensitive currents by nifedipine (5 μM; n=6); and (4) the activation of Ttx-insensitive currents by (+/−) BAY K-8644 (1 μM; n=4) Since Ttx inhibits voltage-gated Na+ channels, and voltage-gated $Ca^{2+}$ channels are inhibited by nifedipine and activated by (+/−)BAY K-8644 these data confirm the presence of voltage-gated $Ca^{2+}$ and Na+ channels in NES 2Y β-cells transfected with $K_{ATP}$ channel submits Panel B shows the appearance of $K_{ATP}$ channels in the NISK 9 β-cell line. See also claim 11 hereinafter.

Figure 18:
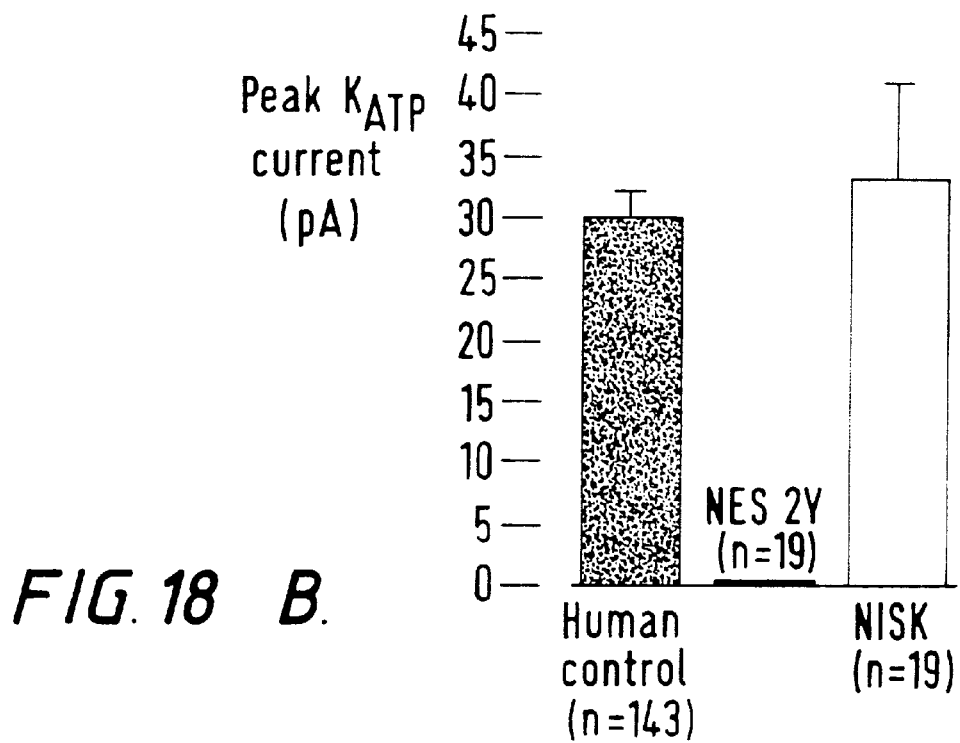
Figure 18:
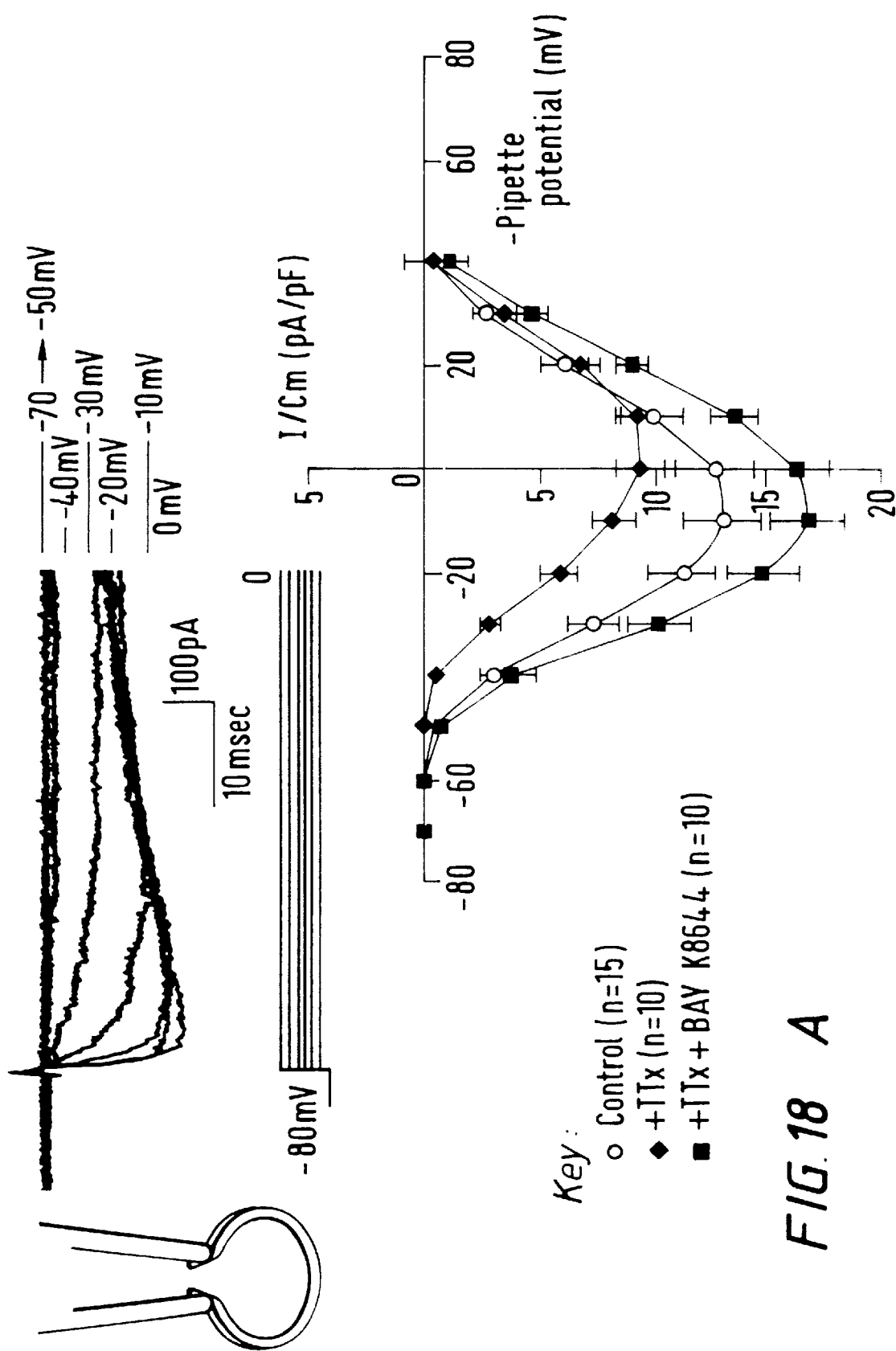

FIG. 18: Voltage-gated ion channels and $K_{ATP}$ channels in human β-cells.

Data obtained using the whole-cell and inside-out variations of the patch-clamp technique. Panel A shows representative voltage-gated currents recorded in human β-cells, and a graphical representation of the relationship between the pipette holding potential and the normalised whole cell current (I=whole-cell current; Cm=cell capacitance) from several recordings. These reveal: (1) the presence of voltage-gated ion channel currents in human β-cells (n=22), (2) the inhibition of voltage-gated currents by tetrodotoxin (Ttx; 313 nM, n=10), and (3) the activation of Ttx-insensitive currents by BAY K 8644 (1 μM; n=10). Panel B shows the mean $K_{ATP}$ channel current in human β-cells, the absence of $K_{ATP}$ channels in NES 2Y β-cell and the appearance of $K_{ATP}$ channels in the NISK 9 β-cell line following transfection. See also claim 11 hereinafter.

Example 1

We selected a neonate patient's pancreas which had the appearance of diffuse nesidioblastosis. The Islets of Langerhans were isolated by a standard method using collagenase digestion, and plated out in non-tissue culture petri dishes (Sterilin). Seven days later the Islets were transferred to T25 culture flasks and allowed to acquire confluency. The cells were then harvested with trypsin/EDTA and plated out in Sterilin dishes again. After 7 days the cells were replated in T25 culture flasks and the cell line derived by continual subculture. Cultures were monitored for human insulin production to help derive an active population. The Islets were plated out into 10 cm Nunc petri dishes using Gibco RPMI 1640 medium containing 11 mM glucose, supplemented with 10% (v/v) fetal calf serum and 2 mM L-glutamine. MIN6, a β-cell line derived from transgenic mice expressing the SV40 large T antigen under the control of the rat insulin promoter were grown in DMEM containing 5 mM glucose, supplemented with 15% heat inactivated myoclone foetal calf serum (Sigma) and 2 mM L-glutamine. MIN6 cells were used between passage 26 and 30 for all experiments.

The control construct pGL-LUC was based on the plasmid pGL2 (Promega), with the thymidine kinase promoter (Tkp) from the herpes simplex virus cloned 5' to the firefly luciferase gene. The construct pGL-LUC200 varies from this in that it contains a −50 to −250 base-pair fragment of the human insulin gene promoter cloned upstream of the Tkp. The IUF1 cDNA was cloned into the pCR3 vector (invitrogen) (to generate pCR3-IUF1) by virtue of the overhanging A's which are the natural result of PCR amplifications with Taq DNA polymerase (Promega).

For western blot analysis, 5 μg samples of nuclear extract were fractionated by SDS-PAGE and blotted on to ECL-nitrocellulose membrane (Amersham) and incubated for 60 minutes in buffer containing 10 mM Tris-HCl, 0.05% (v/v) Tween 20, 0.5 M NaCl, and a 1:1000 dilution of anti-IUF1 antibody. The antibody-antigen complex was then detected by incubating the membrane for a further 60 minutes in buffer containing a 1:5000 dilution of horse-radish peroxidase-conjugated anti-rabbit IgG secondary antibody (ECL-Amersham).

Total RNA was isolated following lysis of cells in 4 M guanidinium isothiocyanate, 0.25 M sodium citrate, 5% (wt/vol) sodium sarcosyl, 0.2 M sodium acetate, pH 4.0. For cDNA synthesis, the RNA sample was heated at 65° C. for 10 minutes, and the transcription reaction performed at 37° C. for 60 minutes in a mixture containing the following: 1×reverse transcriptase reaction buffer (Promega, Southampton, U.K.), 20 units Rnasin (Promega), 40 pmoles driving primer, 0.25 mM dATP, dCTP, dTTP, and dGTP, 25 mM dithiothreitol, 0.5 pg RNA, and 50 units AMV reverse transcriptase (Promega). For quantitative RT-PCR, 10%, 5%, 2.5%, 1%, 0.1% and 0.01% of the total cDNA was amplified with the primers described below, using a 35-cycle PCR with an annealing temperature of 60° C. Twenty percent of the PCR product was then run on an ethidium bromide-stained 1% agarose gel.

Insulin was measured by radioimmunoassay using an anti-guinea pig insulin antibody and $^{123}I$ human insulin (Amersham).

The NES2Y cells were derived from a patient who exhibited sporadic PHHI, with no parental consanguinity and no other affected siblings. The cell line was derived by continual subculture. In keeping with the characteristics of insulin secretion from PHHI Islets in culture, secretion of insulin from the NES 2Y cells was poorly responsive to glucose stimulation (FIG. 1). Glucose-stimulated insulin transcription was also defective in the NES 2Y cells (FIG. 2). This was demonstrated by transfecting the plasmid pGL-LUC200 which contains a −50 to −250 fragment of the human insulin gene promoter into NES 2Y or MIN6 cells. In MIN6 cells the pGL-LUC200 construct gave a five-fold increase in activity in 16 mM glucose compared with 0.5 mM glucose. In NES 2Y cells there was no effect of glucose on the pGL-LUC200 construct. A control vector pGL-LUC which lacked the insulin reporter sequences was unaffected by glucose in both cell types.

Recent studies have demonstrated that glucose activates insulin gene transcription by modulating the phosphorylation state of the transcription factor IUF1. IUF1 binding was therefore examined by EMSA in NES 2Y cells (FIG. 3). Under similar conditions IUF1 binding activity could be detected in MIN6 cells. This was not due to differences in the quality of the nuclear extracts, since the activity of other transcription factors known to bind to the insulin promoter, i.e. IEF1 and USF, could be readily detected in both MIN6 and NES 2Y cells (FIG. 3. IUF1 protein could not be detected by Western Blot analysis in NES 2Y cells (FIG. 4). The 46 kDa form of IUF1 was present in MIN6 cells, but as previously reported, it was absent from the non-insulin expressing cell lines -TC and BHK. The high molecular weight protein (55 kDa) seen in tracks 2 and 3 is always observed in β-cell lines, but does not represent IUF1.

The NES 2Y cells were shown by reverse transcriptase polymerase chain reaction (RT/PCR) to have slightly elevated insulin mRNA levels compared to MIN6 cells, while USF mRNA levels were similar in both cell types (FIG. 5). However, in NES 2Y cells the IUF1 mRNA levels were more than 10-fold less than USF mRNA, and about $10^3$-fold less than insulin mRNA. In MIN6 cells IUF1 and USF mRNA levels were similar, both being about $10^2$-fold less than insulin mRNA levels. These results confirmed that the IUF1 gene was expressed in NES 2Y cells but at very low levels. The sequence of the IUF1 cDNA synthesis from NES 2Y mRNA was identical to the known sequence of human IUF1.

To investigate whether the defect in glucose regulation of the insulin promoter in NES 2Y cells could be corrected by IUF1, a mammalian expression vector harbouring an IUF1 cDNA was co-transfected into NES 2Y cells along with the pGL-LUC and pGL-LUC200 constructs. IUF1 had no effect on the control vector. In the absence of IUF1 glucose had no specific effect on the pGL-LUC200 vector, but in the presence of IUF1 glucose stimulated the pGL-LUC200 activity 5-fold (FIG. 6). Thus a full transcriptional response to glucose could be restored by transfecting the NES 2Y cells with IUF1.

Example 2

Stable co-transfection with cDNA encoding IUF1, SUR1 and Kir 6.2.

cDNAs encoding SUR1 and Kir 6.2 were subcloned into a pIRES vector (Clontech Laboratories, Palo Alto, Calif., USA) allowing expression using an internal ribosome entry site. The human IUF1 cDNA was transfected using the eukaryotic pCR3 expression vector (Invitrogen, Inc.). Cells were liposome transfected, with clones isolated at minimal cell density and selected using 800 ug/ml G418. Of 192 original clones, 40 were expanded, and finally 20 strongly-growing clones were expanded again, and assayed for the glucose sensitivity of insulin release (radioimmunoassay) and the presence of active IUF1 (electrophoretic mobility shift assay, and western blot analysis). Of these clones, NISK5, NISK7 and NISK9 were positive for IUF1, and showed good glucososensitive insulin secretion (in comparison with the NES 2Y parent clone) (FIGS. 7 and 9). These three clones were then expanded, and cultures maintained in RPMI media supplemented with 10% foetal calf serum, and 800 ug/ml G418.

In some PHHI patients the disease has recently been mapped to mutations in the sulphonylurea receptor (SUR) gene. In fact genetic linkage has identified a susceptibility locus for PHHI within a region of chromosome 11 that encodes $K_{ATP}$ channel subunits of which sulphonylurea receptor is one; SUR1 is an ATP-binding cassette protein. The $K_{ATP}$ channel also comprises at least a $K^+$ channel pore Kir 6.2. The $K_{ATP}$ channel that plays an important role in the mechanism whereby glucose metabolism in β-cells is linked to insulin secretion. The significance of the loss of $K_{ATP}$ channel function is that β-cells can no longer adequately control the regulated entry of $Ca^{2+}$ ions which is inextricably linked to the $Ca^{2+}$-dependent release of insulin. Thus, as $K_{ATP}$ channels are critical for the control of glucose-induced electrical responses, unregulated $Ca^{2+}$ influx stimulates $Ca^{2+}$-dependent exocytosis, which underpins insulin hypersecretion. Evidence linking the disease to abnormal $K_{ATP}$ channel activity comes from the observation that cells isolated from parents with PHHI lacked operational channel activity resulting in a loss of glucose-induced insulin secretion. It is noted that a mutation in either SUR1 or Kir 6.2 can result in the onset of PHHI.

However, in addition to stimulating insulin secretion, glucose metabolism also regulates transcription of the insulin gene through modulation of the phosphorylation state and DNA binding activity of the homeodomain transcription factor IUF1, which is also known as IPF1, IDX1, STF1 or PDX1. In the adult, expression of IUF1 is restricted to pancreatic β-cells and somatostatin secreting cells of the duodenum. It binds to the consensus sequence C(T/C)TAAG located at four sites (the A boxes at −77, −129, −210 and −313) in the human insulin gene promoter. IUF1 (PDX1) also plays an important role in lineage determination in the developing pancreas. Because PHHI may be associated with β-cell hyperplasia during fetal development, and since IUF1 is involved not only in linking glucose metabolism to the insulin gene but is also a major regulator of β-cell differentiation during embryogenesis, we concluded that defects in both these processes would explain some of the pathologies associated with PHHI. We have been able to show that expression of IUF1 was impaired in PHHI. Thus cells derived from a patient with PHHI (Nes2Y cells) were lacking in IUF1 (although small amounts of IUF1 mRNA could be detected by using very sensitive RT/PCR), and the insulin gene was unresponsive to glucose. We were then able to reinstate a full stimulatory response of the insulin gene to glucose in the Nes2Y (NesIUF1) cells by stably transfecting them with IUF1. The NesIUF1 cells did not secrete insulin in response to glucose. We have now found that glucose sensitive insulin secretion can be engineered into NesIUF1 cells by stably co-transfecting them with cDNAs encoding SUR1 (the sulphonylurea receptor) and the ATP-sensitive K channel (Kir 6.2). Several clones were obtained (designated Nisk cells after Nes, IUF1, Sur and $K_{ATP}$), three of which, Nisk5, Nisk7 and Nisk9 were found to secrete insulin in response to glucose in the physiological range.

Potential applications for this inventive concept include:
1) Treatment of PHHI. Cells generated from a particular patient can be engineered as above to repair the defect in glucose sensitive insulin secretion and implanted back into the patient of origin. This syngeneic implantation would get round problems of tissue rejection and constitutes a novel form of gene therapy for this disorder.
2) The ability to generate human glucose responsive insulin secreting β-cell lines has positive implications for β-cell research. Their use may potentially be as widespread as HeLa cells. They can be used in drug discovery programmes and in the discovery of factors involved in the induction of β-cell proliferation.
3) The cells would also be transplanted into diabetic patients. This places a significant value on these cells and this approach to the generation of these cells.

The invention relates therefore to an insulin producing cloned human β-cell line and to such a cell line genetically engineered to be glucose responsive within the physiological range, to a method of production thereof, and to an NISK cell line produced by the method of the present invention.

Example 3

Control experiments were performed using isolated human or mouse islets cells prepared as previously described or upon the glucose responsive insulin-secreting cell lines MIN 6 and BRIN BD11; NES 2Y cells were maintained as described previously.

Reporter constructs pGL-LUC and pGL-LUC200, and the pCR3-PDX1 construct were as described previously. pBK-Kir 6.2 was a kind gift from Dr Frances Ashcroft, University of Oxford, as was pSK-SUR1. The SUR1 coding region was blunt ended and subcloned into pIRES$_{neo}$ (Clontech, USA) for expression in the NES 2Y cells. DNA was prepared using the Qiagen Endotoxin-Free Maxiprep method and quantitated spectrophotometrically.

Cells were grown to 80% confluence in six-well plates and were transfected by mixing 4 µg of DNA with 54 µl of a 1 nM lipid suspension containing a 2:1 mixture of dioleoyl-L-α-phosphatidylethanolamine (DOPE), (Sigma) and dimethyl-dioctadecylammonium bromide (DDAB), (Fluka, Germany) in 1 ml of serum free Optimem (Gibco, UK). The lipid DNA complexes were allowed to form for 20 minutes at room temperature before being added to the washed cells. Following 5 hours incubation, 1 ml of complete medium containing 30% heat inactivated myoclone foetal calf serum was added to the cells. After 12 hours, the medium/DNA complexes were replaced by complete medium and the cells left for a further 24 hours. For transient transfection of reporter gene constructs, cells were then harvested and assayed as previously described. For cell lines which had been triple transfected with pCR3-PDX1, pBK-Kir 6.2 and pIRES-SUR1: 48 hours post-transfection, cells were split to 10% cell density in 10 cm petri dishes, in the presence of 800 µg/ml G418 (Fermentas, UK), a dose which promotes toxic cell death in untransfected cells within 12 hours (data not shown). Forty-eight hours later, surviving individual colonies of G418-resistant cells were isolated and transferred to 96-well plates, with individual clones of cells expanded from there to 6-well plates and then to standard 10 cm tissue culture plates, according to viability. Clones were assayed at this stage for insulin secretion, with glucose-responsive clones selected and maintained in culture (800 µg/ml G418). NISK9 β-cells represent one of three glucose-responsive NISK clones isolated from 192 selected cell populations.

All data were obtained from either primary cultured human islet cells (control) or from NES 2Y β-cells (transfected and untransfected) by patch-clamp techniques.

Standard KCl- and NaCl-rich solutions were used in all electrophysiology recordings to provide quasi-physiological cationic gradients. Procedures used for data collection and analysis were described previously. All current traces are displayed with upward deflections representing outward current events.

Ca$^{2+}$ microfluorimetry experiments were performed with fura-2-loaded cells and intact islets as described previously.

Insulin was measured by radioimmunoassay using an anti-human insulin antibody (Linco, UK) and $^{125}$I-human insulin, as previously described.

Northern blotting was performed by preparing the total RNA from NES 2Y cells and NISK9 cells using the Qiagen RNeasy system, according to the manufacturers protocols. 3 mg per sample of total RNA was denatured and separated on a 1.5% agarose/formaldehyde gel and transferred to Hybond-N$^+$ nitrocellulose membrane (Amersham, UK) in 20×SSC (3M NaCl, 0.3M NaCitrate). Filters were baked at 80° C. for 2 hours, and then prehybridized in 5×SSC, 5×Denhardts solution, 0.5% SDS and 20 mg/ml sonicated salmon sperm DNA, at 65° C. for 1 hour. Following the addition of the appropriate probe, filters Were hybridised overnight at 65° C. Actin PDX1, SUR1 and Kir 6.2 cDNA probes were labelled using the Prime-A-Gene system (Promega, UK) according to the manufacturers instructions. 50 mCi of $^{32}$P-dCTP (Amersham, UK) was used to label each probe. Following hybridisation, filters were washed: 2×SSC, 0.1% SDS at room temperature for 10 minutes (twice): 1×SSC, 0.1% SDS at 65° C. for 15 minutes; 0.1×SSC, 0.1% SDS at 65° C. for 15 minutes (twice). Filters were then wrapped in Saran wrap, and autoradiographed.

To obtain lysates for SDS-PAGE and Western blotting, monolayer cultures of NES 2Y, β-cells, NISK 9 β-cells and BRIN BD11 β-cells were rinsed 3 times with ice-cold PBS and then incubated with 4 ml/T25 flask of hypotone buffer (10 mM Tris-HCl, pH 7.4, 10 mM EDTA) supplemented with inhibitors (1.2 mm Pefabloc, 1 mM orthovanadate, 5 μl/ml protease inhibitor cocktail (Sigma, Chem. Co)) for 30 seconds at 4° C. The resulting cell lysates were transferred to Costar 50 ml tubes and passed through a 19 gauge needle to shear the DNA. Another 16 ml hypotone buffer plus inhibitors was added to the lysate and they were subsequently centrifuged for 5 minutes, at 300 g at 4° C. to remove unbroken cells. The supernatants were transferred to tubes suitable for a Beckman 50.2 TI rotor and centrifuged at 40000 rpm, 4° C. for 30 minutes. The pellets were reconstituted in 2% triton X-100 in PBS, containing 1.5 mM Pefabloc and 1 mM orthovanadate. The protein concentration of the supernatant was determined using the Biorad detergent compatible protein assay. Samples were prepared for electrophoresis by adding 2× concentrated loading buffer (250 mM Tris (pH 10.9), 2% 2-mercaptoethanol, 2% SDS, 20% glycerol, 0.01% bromophenol blue) and boiled for 5 minutes. After electrophoresis on 7% gel, according to Laemmli with 15 μg of protein per lane, proteins were transferred to nitro-cellulose membrane with a pore size of 0.45 μm. The blots were blocked in a solution of 5% milk powder in PBS and 0.1% Tween (PBS-T) for 1 hour at room temperature. Thereafter, incubated with anti-SUR1 antibody (kindly provided by Professor Susumu Seino, 1:3000, overnight at 4° C.): with anti-Rabbit-Horse Radish Peroxidase-conjugated antibody (1:2500, 1 h, Amersham, UK) and washed in PBS-T with 1% milk. Antibody binding was visualised by treating the blots with ECL (Amersham, UK) and exposing them to hyperfilm ECL (Amersham, UK).

The lack of operational $K_{ATP}$ channels in NES 2Y cells was documented by direct recordings of electrical activity from both intact cells and isolated patches of cell membrane, FIG. 9. Thus, in intact cells—in marked contrast to control recordings from human β-cells (n=143), there was no spontaneous $K_{ATP}$ channel activity and no response of the cells to the $K_{ATP}$ channel agonist diazoxide (0.5 mM) n=0), FIG. 9A. Similarly, in cell-free patches of membrane isolated from NES 2Y β-cells [in comparison to control β-cell recordings] there was also no spontaneous $K_{ATP}$ channel activity (n=19) (FIG. 9B and FIG. 12B) and no actions of a "cocktail" of nucleotides, potassium fluoride (KF) and diazoxide (FIG. 9B) (n=10). In control cells, the simultaneous addition of ADP (0.1 mM), GDP (0.5 mM), diazoxide (0.2 mM), UDP (0.1 mM) and KF (10 mM) leads to 6±1.7 (n=5) fold increase in $K_{ATP}$ channel activity (FIG. 9B) Finally, the loss of $K_{ATP}$ channel function was also documented by showing that isolated patch formation does not lead to the appearance of $K_{ATP}$ channels despite the loss of intracellular ATP (see FIG. 12 for details).

The consequences of loss of $K_{ATP}$ channels for NES 2Y β-cells are shown in FIGS. 10A, B. Unlike control β-cells, the NES 2Y cells failed to respond through a rise of cytosolic Ca$^{2+}$ concentration ([Ca$^{2+}$]$_i$) when challenged with either glucose (20 mM) (n=17) or the sulphonylurea tolbutamide (0.1–0.2 mM) (n=24) (FIG. 10A). In addition, we saw no action of high external KCl (40 mM) on [ca$^{2+}$]$_i$ (n=23) indicating that NES 2Y β-cells—as has been shown for PHHI β-cells, are unable to govern regulated voltage-dependent Ca$^{2+}$ influx. In PHHI β-cells we have previously shown that there is a causal relationship between loss of ionic control of β-cell function and insulin hypersecretion. This was similarly observed in the NES 2Y β-cells, which in comparison to control cells have elevated rates of insulin release in the absence of stimuli (FIG. 10B). In NES 2Y β-cells both KCl (40 mM) and tolbutamide (0.2 mM) failed to stimulate insulin release since neither agent was able to elevate cytosolic Ca$^{2+}$, but the cells do respond, albeit somewhat poorly, to elevated glucose concentrations (11–16 mM). Collectively each of these findings confirm the loss of function of $K_{ATP}$ channels in the NES 2Y β-cells and the consequences of this for regulated insulin secretion from β-cells.

We have previously shown impaired expression of the transcription factor PDX1 in NES 2Y β-cells by Western blotting and quantitative RT-PCR. The resultant loss of glucose-sensitive insulin gene transcription was measured by comparative activation of the LUC200 reporter gene construct which contains the −50 to −250 region of the human insulin gene promoter.

Since Western immunoblotting with a SUR1 antibody revealed the presence of SUR1 protein in NES 2Y β-cells (FIG. 11A), the loss of $K_{ATP}$ channel function most likely the results from either inappropriate trafficking or incorrect assembly of the SUR1 and Kir 6.2 subunits into an active channel complex at the plasma membrane. In order to correct for the gene defects in K$^+$ channel function and impaired insulin gene transcription factor, NES 2Y β-cells were transfected with cDNA encoding SUR1, Kir 6.2 and PDX1. These cells were designated NISK 9 β-cells. Northern blotting confirmed expression of each of the three trangenes (FIG. 11B), and in both control and NISK 9 β-cells, we found: (i) that Western immunoblotting with SUR1 documented the presence of protein with a distinct profile (the appearance of the associated "smears" probably results from a glycosylated gene product) and (ii) the spontaneous appearance of K$^+$ channels at the plasma membrane, FIG. 12. The overall magnitude of the expressed current was similar to the $K_{ATP}$ channel current recorded from control human β-cells (FIG. 12B) and at the molecular level of the recombinant channels were found to have identical properties to the native β-cell $K_{ATP}$ channel (FIGS. 13, 14). Thus, (i) they undergo spontaneous run-down (FIG. 12A), (ii) elevated concentrations of ATP (0.005–1 mM) cause a concentration-dependent decrease in the number of channel openings (50% inhibition of channels occurring between 5–10 μM ATP (n=4) similar to human β-cell control data (n=4, not shown), FIG. 13B, (iii) the channels are activated by ADP in the presence of inhibitory concentration of ATP (n=4, FIGS. 13A, B), (iv) the current voltage-relationship profile is non-linear with an inward current conductance of approximately 70 pS (which similar to human β-cells; 66 pS] (FIG. 13C) and (v) the pharmacological properties of these channels are identical to native $K_{ATP}$ channels in β-cells i.e. they are activated (either in intact cells or isolated patches) by the agonist diazoxide and inhibited by sulphonylureas such. as tolbutamide (FIG. 14). (In addition, we also found in isolated patches that 0.25 mM tolbutamide inhibited $K_{ATP}$ channels to 40.8±8.5% (n=3) of the control value and 0.2 mM efaroxan to 8.5±5.6% (n=3) of the immediate control value).

Of more notable importance than the successful expression of these channels (FIGS. 12–14) are the consequences that this procedure has for the function of the PHHI-derived β-cells. Unlike NES 2Y cells, NISK 9 β-cells do respond by a rise in cytosolic $Ca^{2+}$ when challenged with either glucose (n=6), tolbutamide (n=21) or KCl (n=20) (FIGS. 16A, B) and this is causally linked to regulated insulin secretion (FIG. 16C). In comparison to NES 2Y β-cells, NISK 9 cells do not constitutively release insulin at. elevated rates, under non-stimulated conditions (0.9±0.1 ng/ml/$10^6$ cells/hr vs 0.1±0.05 ng/ml/$10^6$ cells/hr (FIGS. 10B vs 16B respectively) and as a result of the transfection event, these cells are now fully glucose-responsive over the physiologically relevant range of glucose concentrations, FIG. 16C. Finally, the consequences of $K_{ATP}$ channel restoration and PDX1 expression were analysed at the level of insulin gene transcription and in comparison to the NES 2Y β-cells, NISK 9 cells were found to show normal glucose responsive insulin gene transcription (FIG. 6).

Hence, transgenic expression of SUR1, Kir 6.2 and PDX1 in PHHI derived β-cells has led to the generation of NISK9 β-cells which demonstrate: (i) normal $K_{ATP}$ channel activity, (ii) normal depolarisation-response coupling, (iii) a restoration of cytosolic $Ca^{2+}$ signalling leading to regulated glucose-induced insulin secretion, and (iv) glucose-responsive transcription of the insulin gene.

These studies provide the first characterisation of a glucose-responsive human β-cell line and document the feasibility of in vitro gene therapy for persistent hyperinsulinaemic hypoglycaemia of infancy. Of key important to this study is the availability of proliferating β-cells from the patient with PHHI. The NES 2Y β-cells recapitulate the properties and essential features of insulin-secreting cells isolated from patients with PHHI following pancreatectomy (including the patient who was the source of the tissue). Thus, the NES 2Y β-cells: (1) lack of operational $K_{ATP}$ channels, (2) have markedly impaired cytosolic $Ca^{2+}$ signalling mechanisms, (3) constitutively release insulin at an elevated rate in the absence of stimuli and (4) do not respond to depolarisation-dependent agonists through the release of insulin. These same characteristics have also been recently described in transgenic mice that express defective $K_{ATP}$ channels in β-cells. Thus, as PHHI is a rare condition, the availability of the NES 2Y β-cell is an important asset to ongoing studies of the molecular pathophysiology of the condition.

The loss of $K_{ATP}$ channel in NES 2Y β-cells has a major influence upon regulated insulin release, however, it is clear from the data shown in FIG. 10B that elevated glucose concentrations will cause insulin release. This finding might appear as somewhat unexpected but it can be readily explained through the "$K_{ATP}$ channel-independent" pathway of glucose-induced secretion, one of the glucose "augmentation" routes first described in rodent β-cells and only recently in human β-cells. This pathway, which is uncovered in normal β-cells by pharmacological agents that eliminate the contribution of $K_{ATP}$ channels to the operation of β-cells, accounts for second phase insulin release which in normal cells is dependent upon glucose metabolism and the concomitant entry of $Ca^{2+}$. Thus, in the PHHI-derived cells that lack operational $K_{ATP}$ channels, unregulated $Ca^{2+}$ influx will fuel glucose-induced secretion, as seen in FIG. 10B. Similar findings have also been recently observed in acutely isolated β-cells from a patient with PHHI.

The properties of $K_{ATP}$ channels as expressed in the transgenic NISK 9 β-cells are strikingly similar to those reported in native tissue. Thus, the recombinant channels are inwardly-rectifying, inhibited by cytosolic ATP in a concentration-dependent manner, activated by ADP in the presence of ATP, undergo spontaneous run down in isolated patches, and are moderated by both diazoxide, sulphonylureas, and imidazolines. The operation of these $K_{ATP}$ channels is also clearly important to the function of the NISK 9 β-cells. Not only does the transfection event underpin the development of glucose-responsiveness within a physiologically-relevant concentration range (FIG. 16C) but it also governs both KCl- and tolbutamide-induced increases in the cytosolic $Ca^{2+}$ concentration and insulin-release (FIG. 16) and controls the inhibition of glucose-induced rises in cytosolic $Ca^{2+}$ by diazoxide (FIG. 16A).

In comparison to control recordings, no operational $K_{ATP}$ channels or voltage-operated $Ca^{2+}$ and $Na^+$ channels were documented in the NES 2Y β-cells. See FIGS. 9, 17 and 18. The consequences of this are that the NES 2Y β-cells failed to respond through a rise in cytosolic $Ca^{2+}$ concentration ($[Ca^{2+}]_i$) when challenged with either glucose (20 mM) (n=17), or the sulphonylurea tolbutamide (0.1–0.2 mM) (n=24) (FIG. 10). In addition, we saw no action of a depolarising concentration of high external KCl (40 mM) on $[Ca^{2+}]_i$ (n=23) indicating that NES 2Y β-cells, are unable to govern regulated voltage-dependent $Ca^{2+}$ influx, FIG. 10A. In acutely isolated PHHI β-cells there is a causal relationship between loss of the ionic control of β-cell function and insulin hypersecretion. This was similarly observed in the NES 2Y β-cells, which in comparison to control cells have elevated rates of insulin release in the absence of stimuli (FIG. 10) and both KCl (40 mM) and tolbutamide (0.2 mM) failed to stimulate insulin release since neither-agent was able to. elevate cytosolic $Ca^{2+}$, FIG. 10, NES 2Y cells do, however, respond—albeit somewhat poorly, to elevated glucose concentrations (11–16 mM) through the $K_{ATP}$ channel-independent pathway of glucose augmentation. These findings confirm the loss of function of $K_{ATP}$ channels in the NES 2Y β-cells, and the consequences of this for regulated insulin release.

In the transfected NES 2Y β-cell, $K_{ATP}$ channels were found to be spontaneously operational at the plasma membrane, FIGS. 12–13 and the overall magnitude of the expressed current was similar to the $K_{ATP}$ channel current recorded from control human β-cells, FIG. 12. Surprisingly, transfection of NES 2Y β-cells also led to the appearance of voltage-gated $Na^+$ channels in the β-cell. The appearance of voltage-gated currents was documented by the application of a step depolarising membrane potential change from a holding potential of −80 mV. Under these conditions, macroscopic whole-cell inward currents were recorded from both voltage-gated $Ca^{2+}$ channels and voltage-gated $Na^+$ channels. Inhibitions of the currents by tetrodotoxin (TTx)

confirms the presence of voltage-gated Na$^+$ channels, FIG. 17 whereas the further inhibition of TTx-insensitive currents by nifedipine and their subsequent activation by the agonist BAY K-8644, confirms the operation of voltage-gated Ca$^{2+}$ channels in the NISK 9 β-cell, FIG. 17. Similar data to the NISK 9 β-cells results were also obtained from control human β-cell recordings, FIG. 18.

Collectively this data suggest the appearance of voltage-gated ion channels in β-cells through genetic manipulation of the K$_{ATP}$ channel subunits, and this is supported by functional data which correlates changes in intracellular Ca$^{2+}$ with the release or insulin. Thus unlike, NISK 9 β-cells NES 2Y cells, do not respond by a rise in cytosolic Ca$^{2+}$ when challenged with either glucose (n–6), tolbutamide (n–21) or KCl (n=20) and this is causally linked to regulated insulin secretion. Hence, transgenic expression of SUR1, Kir 6.2 and PDX1 in PHHI derived β-cells has led to the generation of NIKS9 β-cells which demonstrate: (i) normal K$_{ATP}$ channel activity, (ii) normal depolarisation-response coupling events, and (iii) a restoration of cytosolic Ca$^{2+}$ signaling leading to regulated glucose-induced insulin secretion through the operation of voltage-gated Ca$^{2+}$ channels and voltage-gated Na$^+$ channel.

The data are the first to document the successful in vitro gene therapy for PHHI. In addition, the data provide a novel insight into the mechanism of stimulus-secretion coupling for insulin release in β-cells. Glucose-induced closure of K$_{ATP}$ channels has for a long time been recognised to initiate a depolarisation of the cell membrane potential. Our data show that the presence of K$_{ATP}$ channels is also functionally linked to the operation of voltage-gated ion channels; NES 2Y β-cells lack voltage-gated ion channels, whereas NES 2Y β-cells transfected with the K$_{ATP}$ channel subunits express operational voltage-gated Ca$^{2+}$ channels and voltage-gated Na$^+$ channels. One implication of these data is that there is a physical association or coupling between either SUR1 and/or Kir 6.2 with voltage-gated ion channels in β-cells, and this raises the possibility that defects in K$_{ATP}$ channel subunits have a direct rather than an associated impact upon the function of other ion channels. This novel interdependency of function has important implications for not only for our understanding of the regulation of insulin release, and the events that underpin to the onset of metabolically-related diseases but also for the pharmaceutical control of β-cell function in the treatment of PHHI and diabetes. Thus, as a consequence of these findings, we suggest that the modulation of K$_{ATP}$ channels in β-cells has a direct effect upon the function of voltage-gated Ca$^{2+}$ channels and voltage-gated Na$^+$ channels.

Accordingly, the NES 2Y β-cells are a key in vitro model cells for the study of persistent hyperinsulinaemic hypoglycaemia of infancy and the operation of β-cells in the absence of K$_{ATP}$ channel expression. In addition, our data are the first to document successful in vitro gene therapy for a metabolically related disorder and our findings allude to the possibility that in future, following pancreatectomy, acutely isolated β-cells from PHHI patients could be similarly engineered for subsequent autotransplatation. By transgenic manipulation of the NES 2Y β-cells, we have also generated the first fully glucose-responsive human insulin-secreting cell line. In these cells, we have demonstrated the operation of both the "K$_{ATP}$ channel-dependent" (FIG. 16C) and "K$_{ATP}$ channel-independent" (FIG. 10B) pathways of insulin secretion as well as the actions of glucose at a transcriptional level, through the restoration of glucose-responsive transcription of the insulin gene (FIGS. 10C, 16C).

We claim:

1. An immortalized human β-cell line which secretes insulin when contacted by glucose, said cell line being derived from a donor with PHHI wherein the PHHI is caused by defects in genes encoding PDX1 and either SUR1 or Kir6.2.

2. A cell line according to claim 1 derived from Islets of Langerhans taken from a fetus with PHHI.

3. A cell line according to claim 1 which secretes insulin when in contact with glucose which is present in the physiological range of 4 to 10 mM.

4. A cell line according to claim 1 transfected with cDNA encoding PDX1 and stably co-transfected with cDNA encoding SUR1 and cDNA encoding Kir6.2.

5. A cell line according to claim 1 formulated for implantation via encapsulation.

6. A method for producing a human β-cell which secretes insulin when contacted by glucose, said method comprising:
    (a) selecting an unregulated immortalized human insulin secreting β-cell, said cells being derived from a donor with PHHI wherein the PHHI is caused by defects in genes encoding PDX1 and either SUR1 or Kir6.2;
    (b) transfecting said selected cell with cDNA encoding PDX1 and stably co-transfected with cDNA encoding SUR1 and cDNA encoding Kir 6.2; and
    (c) proliferating said transfected cell line.

7. A method according to claim 6 wherein the unregulated immortalized cell line is selected from Islets of Langerhans taken from a fetus or child with PHHI.

8. A NISK9 cell line deposited under No. 09709106 on the Sep. 1, 1997 at The European Collection of Cell Cultures; Centre for Applied Microbiology and Research, Salisbury, Wiltshire, United Kingdom.

9. An immortalized human β-cell line which secretes insulin when contacted by glucose, said cell line being derived from a donor with PHHI wherein the PHHI is caused by defects in genes encoding PDX1 and either SUR1 and Kir6.2 and transfected with cDNA encoding PDX1 and stably co-transfected with cDNA encoding SUR 1 and cDNA encoding Kir6.2.

* * * * *